(12) United States Patent
Brisbois et al.

(10) Patent No.: US 11,103,622 B2
(45) Date of Patent: Aug. 31, 2021

(54) THROMBORESISTANT/BACTERICIDAL S-NITROSO-N-ACETYLPENICILLAMINE (SNAP)-DOPED NITRIC OXIDE RELEASE POLYMERS WITH ENHANCED STABILITY

(71) Applicant: The Regents of the University of Michigan, Ann Arbor, MI (US)

(72) Inventors: Elizabeth J. Brisbois, Ann Arbor, MI (US); Hitesh Handa, Ann Arbor, MI (US); Mark E. Meyerhoff, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 30 days.

(21) Appl. No.: 14/765,828

(22) PCT Filed: Feb. 6, 2014

(86) PCT No.: PCT/US2014/015086
§ 371 (c)(1),
(2) Date: Aug. 4, 2015

(87) PCT Pub. No.: WO2014/124125
PCT Pub. Date: Aug. 14, 2014

(65) Prior Publication Data
US 2015/0366831 A1    Dec. 24, 2015

Related U.S. Application Data

(60) Provisional application No. 61/762,013, filed on Feb. 7, 2013.

(51) Int. Cl.
| | | |
|---|---|---|
| *A61K 31/197* | (2006.01) | |
| *A61L 29/16* | (2006.01) | |
| *A61L 29/08* | (2006.01) | |
| *A61K 31/198* | (2006.01) | |
| *A61K 33/00* | (2006.01) | |
| *A61L 33/04* | (2006.01) | |
| *C08J 5/18* | (2006.01) | |
| *A61L 33/00* | (2006.01) | |
| *C08J 7/046* | (2020.01) | |
| *A61K 9/70* | (2006.01) | |
| *C08J 7/02* | (2006.01) | |
| *C08J 7/06* | (2006.01) | |

(52) U.S. Cl.
CPC ............ *A61L 29/16* (2013.01); *A61K 9/7007* (2013.01); *A61K 31/197* (2013.01); *A61K 31/198* (2013.01); *A61K 33/00* (2013.01); *A61L 29/085* (2013.01); *A61L 33/0082* (2013.01); *A61L 33/0088* (2013.01); *A61L 33/04* (2013.01); *C08J 5/18* (2013.01); *C08J 7/02* (2013.01); *C08J 7/046* (2020.01); *C08J 7/065* (2013.01); *A61K 9/70* (2013.01); *A61L 2300/114* (2013.01); *A61L 2300/404* (2013.01); *C08J 2375/04* (2013.01); *C08J 2383/04* (2013.01)

(58) Field of Classification Search
CPC ............ A61K 9/7007; A61K 9/70; C08J 5/18
See application file for complete search history.

(56) References Cited

U.S. PATENT DOCUMENTS

| | | | |
|---|---|---|---|
| 5,187,305 A * | 2/1993 | Thompson | ............ C07C 323/58 |
| | | | 556/413 |
| 5,665,077 A | 9/1997 | Rosen et al. | |
| 5,994,444 A | 11/1999 | Trescony et al. | |
| 6,171,232 B1 | 1/2001 | Papandreou et al. | |
| 6,656,217 B1 | 12/2003 | Herzog, Jr. et al. | |
| 6,780,849 B2 | 8/2004 | Herrmann et al. | |
| 7,417,109 B2 | 8/2008 | Stamler et al. | |
| 7,425,218 B2 | 9/2008 | Keefer et al. | |
| 7,763,283 B2 | 7/2010 | Batchelor et al. | |
| 7,829,553 B2 | 11/2010 | Arnold et al. | |
| 8,211,459 B2 | 7/2012 | Oh-Lee et al. | |
| 2002/0094985 A1 | 7/2002 | Herrmann et al. | |
| 2006/0039950 A1 | 2/2006 | Zhou et al. | |
| 2009/0182111 A1 | 7/2009 | Padsalgikar | |
| 2009/0255536 A1 | 10/2009 | Av-Gay et al. | |
| 2010/0076162 A1 | 3/2010 | Ameer et al. | |
| 2010/0112033 A1 | 5/2010 | Ganzarolli et al. | |
| 2010/0285100 A1 | 11/2010 | Balkus, Jr. et al. | |
| 2010/0303891 A1 | 12/2010 | Lee et al. | |

FOREIGN PATENT DOCUMENTS

| | | |
|---|---|---|
| JP | 2010155095 | 7/2010 |
| JP | 2010537008 | 12/2010 |
| WO | WO01/70199 A1 | 9/2001 |
| WO | WO2005/003032 | 1/2005 |
| WO | WO2007/012165 | 2/2007 |

(Continued)

OTHER PUBLICATIONS http://www.merriamwebster.com/dictionary/derivative retrieved on Jan. 25, 2011.*

(Continued)

*Primary Examiner* — James W Rogers
(74) *Attorney, Agent, or Firm* — Dierker & Kavanaugh, P.C.

(57) ABSTRACT

A polymeric film includes a polymer matrix having at least one of a discrete RSNO adduct or a polymeric RSNO adduct associated therewith, by: covalent attachment to the polymer matrix; dispersion within the polymer matrix; or both, with the at least one of the discrete RSNO adduct or the polymeric RSNO adduct capable of releasing nitric oxide (NO). The polymer matrix is a polyurethane polymer matrix, a silicone rubber polymer matrix, or a copolymer matrix of polyurethane and silicone rubber. The polymeric film is to exhibit stability under dry conditions at 37° C. and prolonged and controllable NO release rates, when exposed to moisture or light capable of photolyzing an RSNO bond, for a predetermined amount of time from the at least one of the discrete RSNO adduct or the polymeric RSNO adduct.

9 Claims, 13 Drawing Sheets

(56) References Cited

FOREIGN PATENT DOCUMENTS

| WO | WO2007/149520 | 12/2007 |
|----|---------------|---------|
| WO | WO2008/024131 | 2/2008  |
| WO | WO2009/131931 | 10/2009 |
| WO | WO2010/054316 | 5/2010  |
| WO | WO2012/118829 | 9/2012  |

OTHER PUBLICATIONS

Hien Duong, et al., "Intracellular Nitric Oxide Delivery from Stable NO-Polymeric Nanoparticle Carriers", Chemical Communications, Nov. 2013, vol. 49 pp. 4190-4192.
Brandon J. Heilman, et al., "Light-Triggered Eradication of Acinetobacter Baumannii by Means of NO Delivery from a Porous Material with an Entrapped Metal Nitrosyl" JACS, 2012, Issue 134, pp. 11573-11582.
Hidemasa Katsumi, et al. "Development of Polyethylene Glycol-Conjugated Poly-S-Nitrosated Serum Albumin, a Novel S-Nitrosothiol for Prolonged Delivery of Nitric Oxide in the Blood Circulation in Vivo", The Journal of Pharmacology and Experimental Therapeutics, 2005, vol. 314, No. 3, pp. 1117-1124.
Mowery, Kelly et al., "Preparation and characterization of hydrophobic polymeric films that are thromboresistant via nitric oxide release", Biomaterials, 2000, vol. 21, Iss. 1, pp. 9-21.

\* cited by examiner

S-nitroso -N-acetyl - D,L - penicillamine
(SNAP)

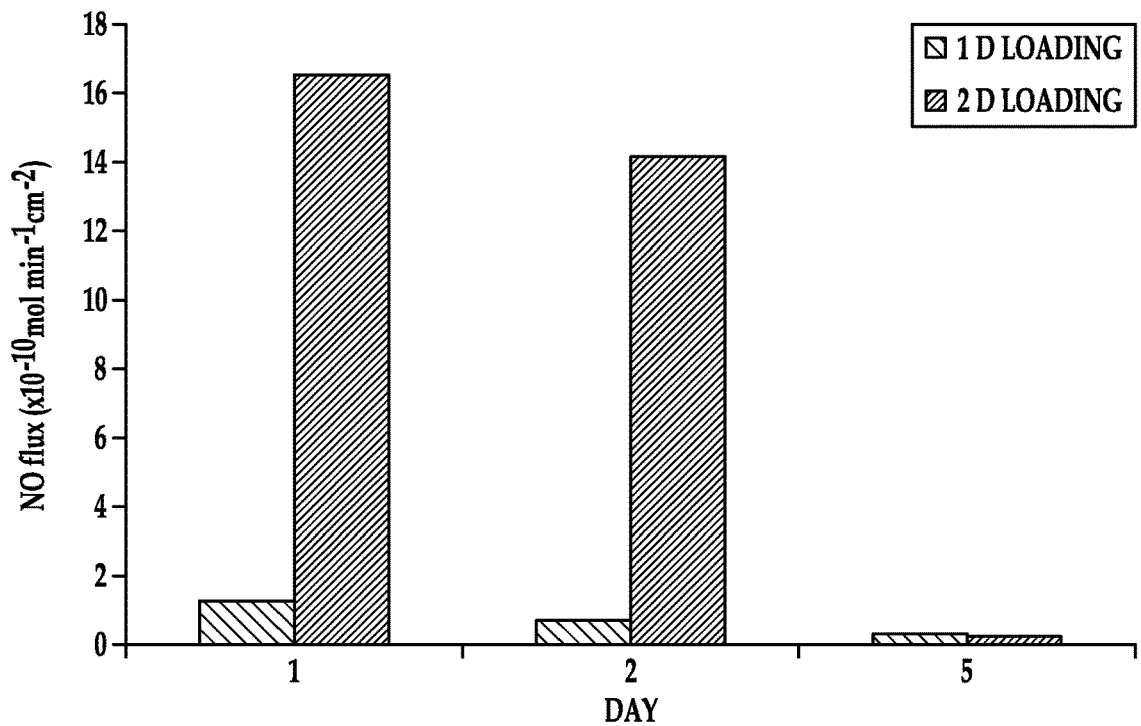
FIG. 15
SNAP / E2As CATHETERS
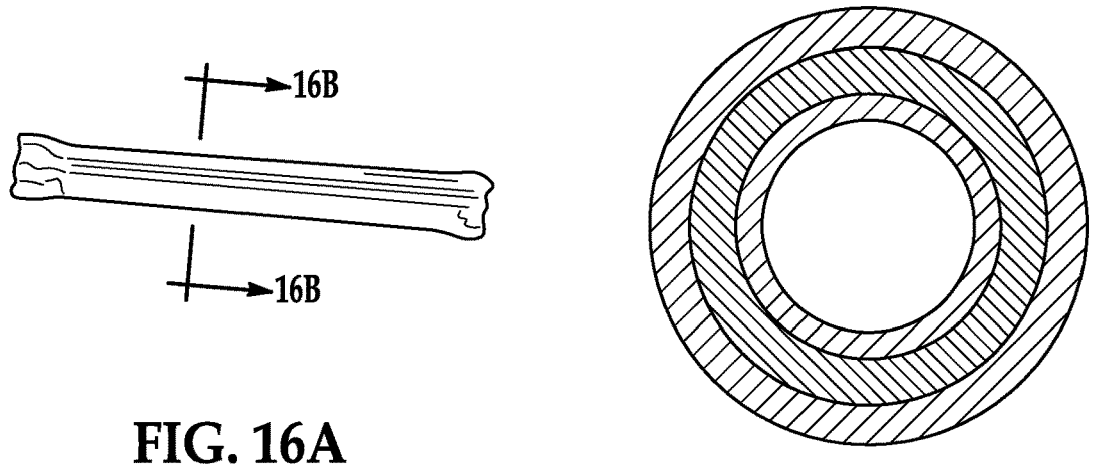
FIG. 16A
FIG. 16B

THROMBORESISTANT/BACTERICIDAL S-NITROSO-N-ACETYLPENICILLAMINE (SNAP)-DOPED NITRIC OXIDE RELEASE POLYMERS WITH ENHANCED STABILITY

CROSS-REFERENCE TO RELATED APPLICATIONS

This application claims the benefit of U.S. Provisional Application Ser. No. 61/762,013, filed Feb. 7, 2013, which is incorporated by reference herein in its entirety.

STATEMENT REGARDING FEDERALLY SPONSORED RESEARCH OR DEVELOPMENT

This invention was made with government support under EB004527 and EB000783 awarded by the National Institutes of Health. The government has certain rights in the invention.

BACKGROUND

Nitric oxide (NO) has been shown to have several important physiological functions, including its unique vasodilating properties, cancer-fighting potency, antibacterial properties, and anti-platelet activity. Although NO is a stable radical, it may be highly reactive with hemoglobin and oxygen, thus making delivery of NO to the target site challenging. Stable hydrophilic, as well as hydrophobic NO donors may be best to take advantage of the potency of NO for a wide range of biomedical applications. These include NO-releasing pharmaceuticals and the preparation of thromboresistive hydrophobic polymeric coatings for medical devices such as intravascular catheters and extracorporeal circuits (based on NO's antiplatelet activity). However, despite the benefits of NO, the use of NO donors in polymeric systems has been relatively limited for various reasons.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

(FIG. 3A) or 37° C. (FIG. 3B) (the data is the mean±SEM (n=3));

FIG. 15 is a graph showing an NO release profile of polyurethane tubing (a micro-polyurethane tubing available from Scientific Commodities, Inc.) impregnated with SNAP, the tubing having been soaked in a SNAP/acetone solution for either 1 or 2 days;

FIG. 16A is a schematic illustration of a catheter tubing coated with an active layer of 5 wt % or 10 wt % SNAP/E2As followed by a top coat of E2As;

FIG. 16B is a cross-sectional view of the catheter tubing of FIG. 16A, taken along line 16B-16B of FIG. 16A;

DETAILED DESCRIPTION

Figure 1A:
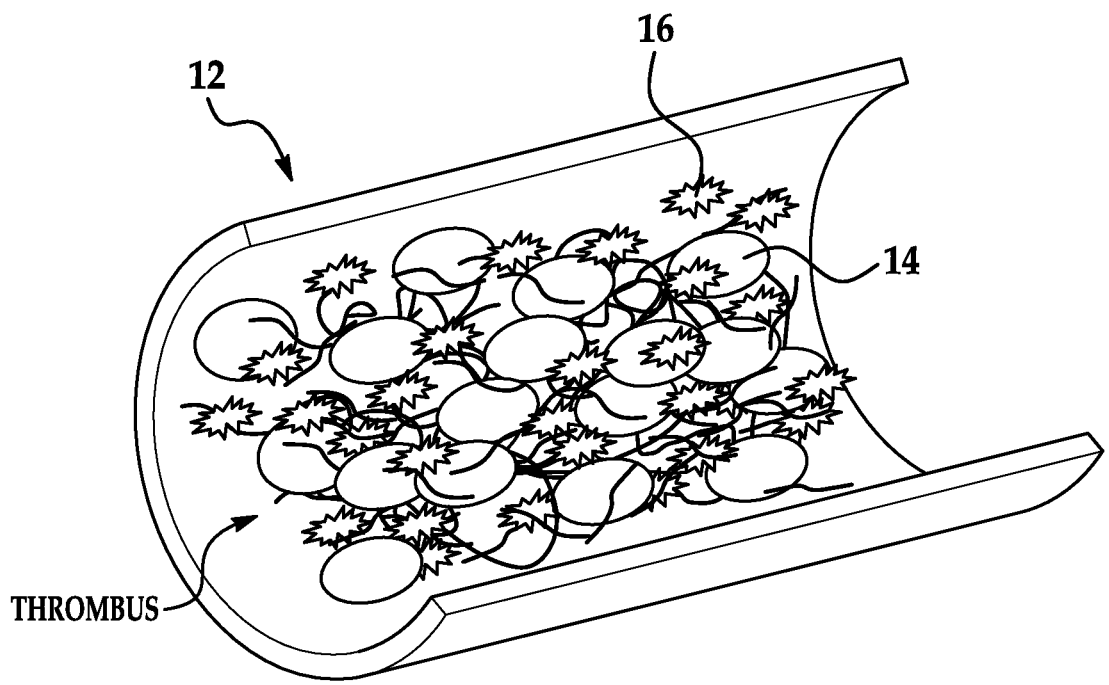
FIG. 1A is a schematic cut-away view showing thrombus formation on a siloxane-based polyurethane elastomer (e.g., Elast-Eon™ E2As) control coated extracorporeal circulation (ECC) circuit.
Figure 1B:
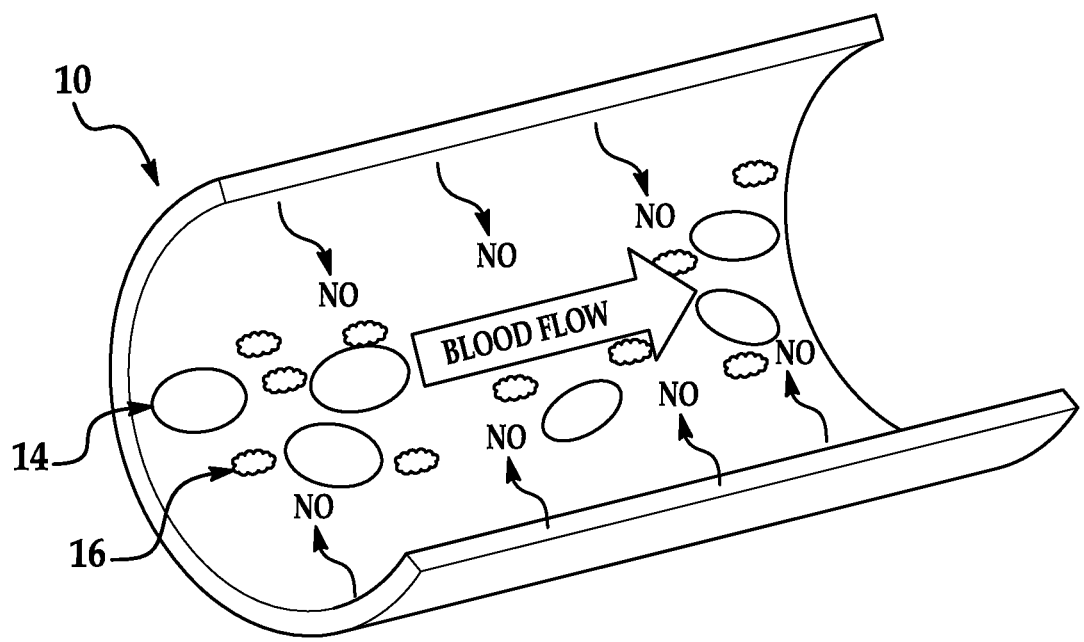
FIG. 1B is a schematic cut-away view showing a S-nitroso-N-acetylpenicillamine (SNAP)/E2As coated ECC circuit, which releases nitric NO and reduces thrombus formation.

Examples according to the present disclosure include a novel RSNO-doped polymer formulation useful for making biomedical devices. The novel polymer formulations form homogeneous films and exhibit RSNO stability even at 37° C. for 4 months (with only about a 10%-15% loss of NO). The novel polymer formulations may be used as coatings to prevent thrombus (i.e., blood clot) formation in, e.g., extracorporeal circulation (ECC) circuits. FIG. 1A is a schematic cut-away view showing a siloxane-based polyurethane elastomer (e.g., Elast-Eon™ E2As) control coated ECC circuit 12 that exhibits thrombus formation. As illustrated, the red blood cells 14 and platelets 16 clot together. In contrast, FIG. 1B is a schematic cut-away view showing an example 10 according to the present disclosure of a SNAP-doped siloxane-based polyurethane elastomer (e.g., SNAP/E2As) coated ECC circuit that does not exhibit thrombus formation. As depicted in FIG. 1B, NO is generated, which contributes to the red blood cells 14 and platelets 16 not clotting together.

Blood/material interaction is important to the success of implantable medical devices, ranging from simple catheters, stents and grafts, to complex extracorporeal artificial organs that are used in thousands of patients every day. Thrombosis is one of the primary problems associated with clinical application of blood contacting materials. Despite a thorough understanding of the mechanisms of blood-surface interactions and decades of bioengineering research effort, the ideal non-thrombogenic prosthetic surface remains an unsolved problem. Over the last 50 years, much has been learned about surface-induced thrombosis and attempts to prevent it with systemic anticoagulation and surface modifications. Surface modifications have included using pure, very smooth silicone rubber or polyurethane, pre-exposure of the surfaces to albumin and other coating proteins, and surface binding of heparin in an ionic as well as a covalent fashion. Despite extensive research to develop a non-thrombogenic surface that mimics the endothelium, none of these modifications have been successful.

Nitric oxide (NO) has been found to be one of two potent vasodilators secreted by normal endothelium that has the ability to inhibit platelet adhesion/activation and aggregation to the blood vessel wall. The NO-flux from a normal and stimulated endothelium has been estimated to be in the range of $0.5 \times 10^{-10}$ mol cm$^{-2}$ min$^{-1}$ to $4 \times 10^{-10}$ mol cm$^{-2}$ min$^{-1}$. Nitric oxide has been extensively studied for its inhibitory effects on circulating platelet and monocyte activation that leads to aggregation and ultimately initiation of thrombosis. A wide range of NO donors such as S-nitrosothiols (RS-NOs), N-Hydroxy-N-nitrosoamines, N-diazeniumdiolates and nitrosyl metal complexes have been studied at least over the past decade.

Nitric oxide (NO) can be released from an NO adduct/donor species appended to polymers within a polymer coating. "Nitric oxide adducts" (NO adducts) and "NO-donors" refer to compounds and functional groups which, under physiological conditions, can donate and/or release NO such that biological activity of the NO is expressed at the intended site of action/target site.

Some examples according to the present disclosure include the NO donor/adduct within a polymer coating. The NO donor/adduct may be integrated into the polymer coating in any suitable manner, an example of which is doping. Suitable NO adducts (examples of which include discrete adducts) are generally those exhibiting capability of embedding (either by covalent attachment and/or dispersion) into the polymer matrix and exhibiting process preparation stability.

"Discrete NO adducts" as referred to herein are those NO adducts (examples of which are RSNOs) which, when placed into a polymer matrix, release therapeutically relevant fluxes of NO, ranging from about $0.2 \times 10^{-10}$ mol cm$^{-2}$ min$^{-1}$ to about $20 \times 10^{-10}$ mol cm$^{-2}$ min$^{-1}$ of NO from the polymer phase. Those compounds that have their NO-releasing moiety covalently attached to a polymer backbone are generally referred to as "polymeric NO adducts." Examples of suitable polymeric NO adducts include, but are not limited to, S-nitrosothiolated polyurethanes, S-nitrosothiolated silicone rubbers, and/or mixtures thereof. Some examples of the discrete NO adducts exhibit some lipophilicity, but may be made more lipophilic by derivatization with one or more alkyl groups.

As such, examples of the present disclosure are novel nitric oxide (NO) releasing coatings formed from polymers doped with S-nitroso-N-acetylpenicillamine (SNAP) to prevent thrombus formation in, e.g., extracorporeal circulation (ECC) circuits and catheter tubing.

Various hydrophobic polymer materials may be employed in examples of the material, method, and device as disclosed herein. These include, but are not limited to materials such as polyurethanes (PU), silicone rubbers (SR), copolymers of polyurethane and silicone rubber (e.g., E2A), poly(vinyl chloride) (PVC), polymethacrylates, polyacrylates, polycaprolactones, and/or mixtures thereof. In other examples, the polymer material may include both hydrophobic and hydrophilic domains. The polymer of choice will be one capable of releasing NO from, for example, covalently attached and/or dispersed S-nitrosothiol (RSNO) type NO-adducts within the polymer. The polymer of choice may also depend upon the application in which polymer coating/film will be used and the desired NO release rate for that application. As examples, a polymer having higher water uptake may be suitable in applications where quick NO release is desirable, while a polymer having lower water uptake may be suitable in applications were slow NO release is desirable. In instances where prolonged NO release is desirable, poly(lactic-co-glycolic acid) (PLGA) additives may also be included in the polymer coating/film to create an acidic environment to further stabilize the RSNO species.

Further, a system is contemplated as being within the purview of the present disclosure that includes discrete RSNOs doped into a polymer, with the polymer also having RSNO appended thereto (e.g., by covalent attachment). For example, previously prepared polyurethane polymers with appended RSNO functional groups can be mixed with discrete RSNOs or similar species to create the long-term NO release polymers enabled by the present disclosure.

In some examples, the NO adduct of choice is one capable of spontaneous release of NO when the polymer is exposed to solutions and/or blood under physiological conditions. In other examples, the NO adduct of choice is one capable of spontaneous release of gas phase NO when the polymer is exposed to certain light conditions. Some examples of NO adducts include discrete S-nitrosothiols (RSNOs).

It is believed that examples of the present disclosure including SNAP doped into siloxane-based polyurethane elastomers (one example of which is E2As) may help stabilize the RSNO adduct, thus advantageously allowing longer NO release from the RSNO species and enhanced storage stability, even at higher temperatures (e.g., 37° C.).

Spontaneous release of NO from the polymer may be governed by at least one process occurring between the NO adduct and the surrounding environment. For RSNO species, these include, but are not limited to temperature, moisture, and the presence of certain wavelengths of light. For example, photolysis of the S—N bond in the RSNO species liberates NO gas. Photolysis can occur with light in either the 300 nm to 400 nm wavelength range or the 500 nm to 600 nm wavelength range. In this example, the efficiency of NO release is generally greater in the higher wavelength range.

Figure 2A:
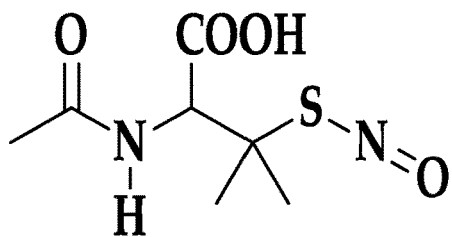
FIG. 2A shows the structure of S-nitroso-N-acetylpenicillamine (SNAP)

It is to be understood that discrete nitric oxide adducts may be either covalently attached to the polymer matrix or may be dispersed therein, or both. Some examples of discrete RSNOs include, but are not limited to S-nitrosoglutathione (GSNO), S-nitroso-N-acetylpenicillamine (SNAP, shown in FIG. 2A), S-nitrosocysteine (CysNO), etc., and derivatized discrete RSNOs. Derivatized RSNOs may be modified with alkyl group(s). As examples, a derivative may have an alkyl group attached to the free carboxyl group of SNAP and/or may have a longer alkyl (i.e., longer than acetyl) attached to the amine group of S-nitrosopenicillamine. As an example, an ester linkage may be formed between the desired alkyl group and the free carboxyl group of SNAP. As another example, a long chain alkyl (including from 4 to 10 carbon atoms) may replace the acetyl group of SNAP so that the long chain alkyl is attached to the amine nitrogen. As other examples, a sugar may be attached to the carboxyl group of SNAP (e.g., glucose-SNAP, mannose-SNAP, fructose-SNAP, etc.).

The SNAP-doped NO release siloxane-based polyurethane elastomer coatings according to examples of the present disclosure were evaluated in vitro and within a short-term in vivo rabbit model of thrombogenicity. The novel coatings according to examples of the present disclosure continuously released from 0.5 to $1 \times 10^{-10}$ mol cm$^{-2}$ min$^{-1}$ NO for 20 days in the dark, soaking at 37° C. in PBS. Additionally, the novel coatings retained about 78% of the SNAP after 4 months at 37° C. in the dark (i.e., not exposed to wavelengths that could photolyze RSNO bonds) and in dry conditions (i.e., in the presence of a desiccant). As discussed further herein, examples of the novel coating materials were employed as inner wall coatings of extracorporeal circuits used for 4 hours of extracorporeal circulation (ECC) in a rabbit model of thrombogenicity to examine the effect of the coatings on platelet function, clotting and fibrinogen adsorption. The SNAP-doped NO release coatings were also used to fabricate catheters, which were implanted in sheep veins for 7 days to evaluate the effects on thrombus and bacterial adhesion.

As mentioned above, nitric oxide (NO) is an endogenous gas molecule that plays several key physiological roles, including prevention of platelet adhesion and activation, inhibiting bacterial adhesion and proliferation, enhancing vasodilation, promoting angiogenesis, and aiding in wound healing. The effects of NO are highly dependent on the location of the NO and its concentration in the physiological system. For example, endothelial cells that line the inner walls of healthy blood vessels produce an estimated NO surface flux ranging from 0.5 mol cm$^{-2}$ min$^{-1}$ to $4.0 \times 10^{-10}$ mol cm$^{-2}$ min$^{-1}$. The function of many blood-contacting devices, including vascular grafts, stents, intravascular sensors, intravascular catheters, and extracorporeal life support circuits, can be impaired due to platelet activation and thrombus formation. One approach to improve the hemocompatibility of such devices is the use of coating materials that mimic the endothelial cells with respect to NO release. Indeed, in recent years there has been considerable interest in developing NO-release and NO-generating materials that can be used to improve the biocompatibility of such devices.

Nitric oxide also exhibits antimicrobial activity, including killing bacteria and preventing biofilm formation. Bacterial infections and biofilm formation are problems that can cause complications with biomedical devices. Bacteria also possess the ability to form biofilms on surfaces when the organism secretes a polysaccharide matrix in which the bacteria will live. This matrix provides both nutrients and protection against the host defense and antibiotics. Biofilms can act as a source of chronic infection, thereby prolonging the recovery time. Among its many biological roles, nitric oxide functions as an antimicrobial agent and as an accelerant to the wound healing process. Nitric oxide has broad-spectrum antibacterial properties, killing both gram-positive and gram-negative bacteria. Low levels of nitric oxide are also reported to efficiently disperse biofilms that have formed on the surface of indwelling medical devices.

Figure 2B:
FIG. 2B shows a scheme of S-nitrosothiol (RSNO) decomposition, which can be catalyzed by metal ions (e.g., $Cu^+$), light, and heat, yielding the disulfide (RSSR) product and nitric oxide (NO)

Nitric oxide is highly reactive under physiological conditions, and thus a wide range of NO donor molecules with functional groups that can store and release NO have been studied for potential biomedical applications. Such molecules include organic nitrates, metal-NO complexes, N-diazeniumdiolates, and S-nitrosothiols (RSNOs). Physiological RSNOs, such as S-nitrosohemoglobin and S-nitrosoglutathione (GSNO), are considered an endogenous reservoir of NO in vivo. Other synthetic RSNOs, such as S-nitroso-N-acetyl-L-cysteine (SNAC) and S-nitroso-N-acetylpenicillamine (SNAP, FIG. 2A) have been shown to exhibit significant antimicrobial and antithrombotic effects. It has also been demonstrated that RSNOs are both vasodilators and potent inhibitors of platelet aggregation. RSNOs undergo thermal decomposition, releasing NO and producing a corresponding disulfide species (RSSR), as shown in FIG. 2B. The NO release from RSNOs can be catalyzed by metal ions (e.g., Cu$^+$) and by light, through the irradiation at energies that correspond to the S-nitroso absorption bands at 340 nm and/or 590 nm. It has been suggested that the more potent activity of RSNOs vs. NO as antiplatelet agents arises from the enhanced stability of RSNOs vs. NO, and generation of NO from RSNOs locally at the surface of platelets by membrane proteins that contain catalytic sites to convert RSNO to NO.

Incorporation of RSNOs into polymers can extend the utility of these NO donors to be applicable as coatings in biomedical devices, providing localized NO release at the blood/device interface. Several NO-release polymers consisting of small-molecule RSNOs dispersed in various polymer matrices, including polyethylene glycol (PEG), poly (vinyl alcohol), poly(vinyl pyrrolidone), and Pluronic® F127 hydrogel, have been suggested. These materials have potential applications for topical NO delivery on wounds via the diffusion of the hydrophilic RSNOs from the polymer to the tissue. In fact, daily application of a GSNO-containing hydrogel has been shown to accelerate the wound healing process. However, the rapid leaching of the RSNOs from such polymers can significantly shorten the NO/RSNO release lifetime, lasting only several hours. An alternate approach has been to synthesize RSNO-modified materials, where the RSNO functionality is covalently bound to the matrix. Fumed silica particles, dendrimers, polyurethanes, polyesters, polydimethylsiloxane (PDMS), xerogels, self-assembled monolayers, and poly(vinyl methyl ether-co-maleic anhydride) (PVMMA) have all been modified with RSNO functionalities. RSNO-modified xerogels were found to release NO for up to 14 days and exhibit reduced platelet and bacterial adhesion. However, such RSNO-modified xerogels suffer from synthesis complications leading to cracking and non-uniform films, low RSNO conversion efficiency (maximum of 40% for the tertiary RSNO-modified xerogels), and thermal instability at room temperature that would limit their shelf-life. Many of the other RSNO modified materials reported to date exhibit both thermal and photoinitiated NO release, but many of these materials have not proven clinically useful due to their limited NO release lifetimes or lack of the RSNO functionality stability during storage, or low conversion to RSNO during synthesis.

Another approach reported to achieve localized NO delivery at a polymer/blood interface is to use NO-generating coatings, in which immobilized catalysts (Cu(I/II) or organoselenium species) can generate NO from endogenous RSNOs. For example, a NO generating coating containing $Cu^0$ nanoparticles was evaluated recently using a rabbit model for extracorporeal circulation (ECC). However, to achieve good efficacy in reducing thrombus formation, continuous infusion of SNAP was required to supplement the endogenous RSNO levels.

In order to avoid the continuous infusion of RSNO species, the present disclosure includes several biomedical polymers that are capable of storing RSNO species. The RSNO-doped coatings according to the present disclosure can advantageously release NO, as well as potentially supplement the endogenous RSNO levels, if NO generating catalysts are also employed.

In the present disclosure, five biomedical grade polymers doped with S-nitroso-N-acetylpenicillamine (SNAP) were investigated for their potential to control the release of NO from the SNAP within the polymers, and further control the release of SNAP itself. As discussed further herein, SNAP is quite stable in the Elast-Eon™ E2As polymer, creating a homogeneous coating that can locally deliver NO (via thermal and photochemical reactions) as well as slowly release SNAP. E2As is an example of suitable siloxane-based polyurethane elastomers contemplated as being within the purview of the present disclosure. E2As is a solution grade of E2A (see Table 1 below). The E2As polymer containing SNAP was coated on the walls of extracorporeal circuits (ECC) and exposed to 4 hour blood flow in a rabbit model of extracorporeal circulation to examine the effects on platelet count, platelet function, clot area, and fibrinogen adsorption. After 4 hours, platelet count was preserved at 100±7% of baseline for the SNAP/E2As coated loops, compared to 60±6% for E2As control circuits (n=4). The SNAP/E2As coating also reduced the thrombus area when compared to the control (2.3±0.6 and 3.4±1.1 $cm^2$, respectively). As will be discussed further herein, the SNAP/E2As catheters were also able to significantly reduce the thrombus area and bacterial adhesion after 7 day implantation in sheep veins. All of the results suggest that the new SNAP/E2As coatings have potential to improve the thromboresistance of intravascular catheters, grafts, and other blood contacting medical devices.

The present inventors also examined the five biomedical polymers (silicone rubber (SR), Elast-Eon™ E2As (a siloxane-base polyurethane elastomer commercially available from Aortech Biomaterials, Scoresby Victoria, Australia), CarboSil® (a thermoplastic silicone-polycarbonate-urethane commercially available from DSM Biomedical Inc., Berkeley, Calif.), Tecoflex™ SG80A and Tecophillic™ SP-60D-60 (both polyurethanes commercially available from The Lubrizol Corporation, Wickliffe, Ohio)) for their potential to act as a storage reservoir for SNAP. The Elast-Eon™ polymer has excellent intrinsic biocompatibility and biostability properties, and exhibits low levels of blood protein adsorption. Each of the SNAP-doped polymers is characterized for its in vitro NO/SNAP release. The present inventors have found that SNAP itself is stable for at least 4 months in the Elast-Eon™ E2As polymer, creating a coating that releases NO thermally (at physiological temperature) and can also serve as a reservoir to supplement endogenous RSNO levels (by SNAP diffusion into blood from the polymer). The new SNAP/E2As polymer was tested for potential biomedical applications via, e.g., an ECC rabbit model of thrombogenicity to assess preservation of platelet count and function, and thrombus area after 4 hours of ECC.

It is to be understood that other siloxane-based polyurethane elastomers (aside from E2As) are also contemplated as being suitable for use in the present disclosure. Further, it is to be understood that other grades of Elast-Eon™ siloxane-based polyurethane elastomers (commercially available from Aortech Biomaterials, Scoresby Victoria, Australia) are contemplated as being suitable for use in the present disclosure. Table 1 below is a table of properties of various grades of Elast-Eon™ polymers. In addition to those examples shown in Table 1, it is believed that other suitable polymers include CarboSil®, PuriSil™, or silicone rubber.

TABLE 1

| | Elast-Eon ™ Properties | | | | | | | |
|---|---|---|---|---|---|---|---|---|
| TEST | E5-130 | E5-325* | E2A* | E2-945 | E2-852 | E2-860 | E2-862 | E4 |
| Durometer Hardness | 77A | 82A | 90A | 50D | 55D | 65D | 68D | 80D |
| Tensile Strength, MPa | 21 | 23 | 26 | 28 | 30 | 34 | 34 | 60 |

TABLE 1-continued

Elast-Eon™ Properties

| TEST | E5-130 | E5-325* | E2A* | E2-945 | E2-852 | E2-860 | E2-862 | E4 |
|---|---|---|---|---|---|---|---|---|
| Elongation at Break, % | >700 | >500 | >450 | >400 | >300 | >200 | >200 | 25 |
| Tensile Stress, 100% E, MPa | 4 | 5 | 8 | 12 | 15 | 23 | — | — |
| Tensile Stress, 200% E, MPa | 5 | 7 | 10 | 15 | 18 | — | — | — |
| Tensile Stress, 300% E, MPa | 6 | 9 | 13 | 18 | 23 | — | — | — |
| Modulus of Elasticity, MPa | 11 | 15 | 35 | 115 | 360 | 650 | 650 | — |
| Tear Strength, kN/m | 45 | 60 | 80 | 97 | 129 | — | — | — |
| Physical Form | Pellets | Pellets** | Pellets** | Pellets | Pellets | Pellets | Pellets | Pellets |
| Melt Temperature ° C. | 175-185 | 180-185 | 195-200 | 220 | 210-215 | 210-215 | 210-215 | 185 |

*Can also be supplied in solution grade and is soluble in both THF and DMAc.
**Also supplied in dispersion form.

Preliminary In Vitro Characterization of Various SNAP-Doped Polymer Films

SNAP doped into all of the five biomedical polymers produced homogeneous and transparent films of green color, without any observable phase separation. The 10 wt % SNAP films stored approximately 0.42 μmol of SNAP per mg polymer film (or 6 μmol/cm$^2$), while the 5 wt % SNAP films stored approximately 0.21 μmol of SNAP per mg polymer film (or 3 μmol/cm$^2$).

Figure 3A:
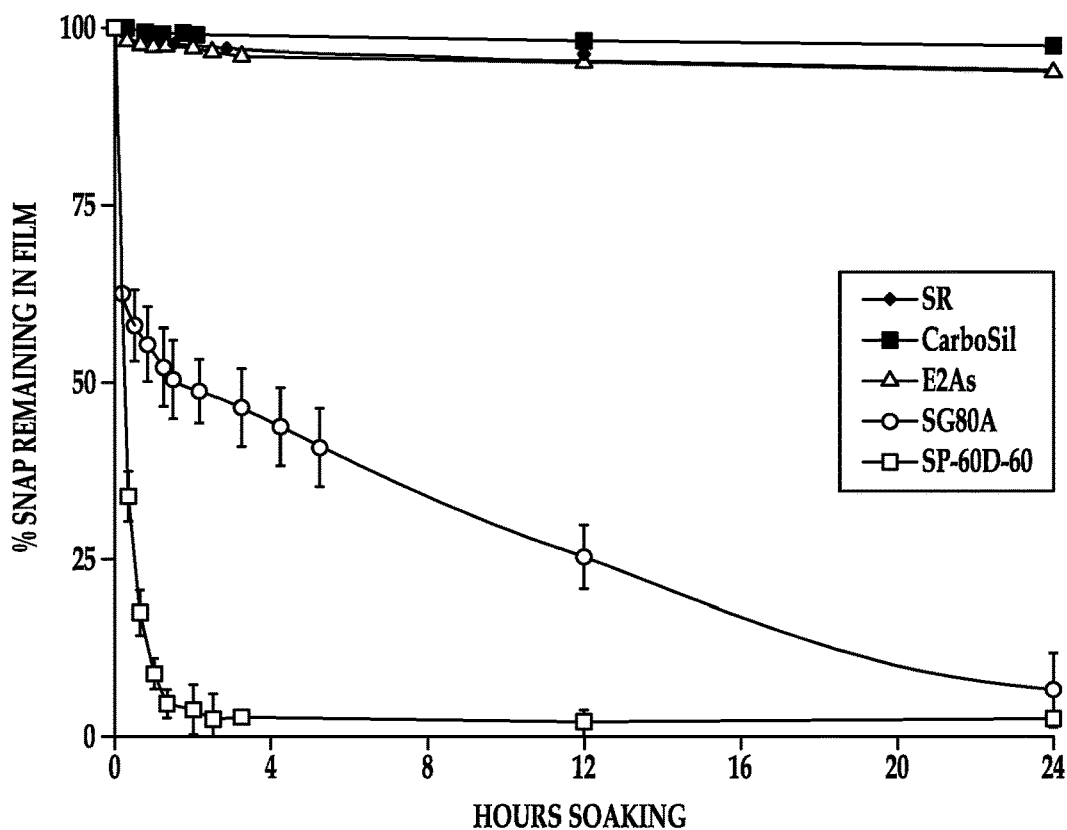
FIGS. 3A and 3B show diffusion of SNAP from various polymer films containing 10 wt % SNAP, monitored at 340 nm, films were immersed in 4 mL phosphate buffered saline (PBS) in the dark at room temperature, 22° C.
Figure 3B:
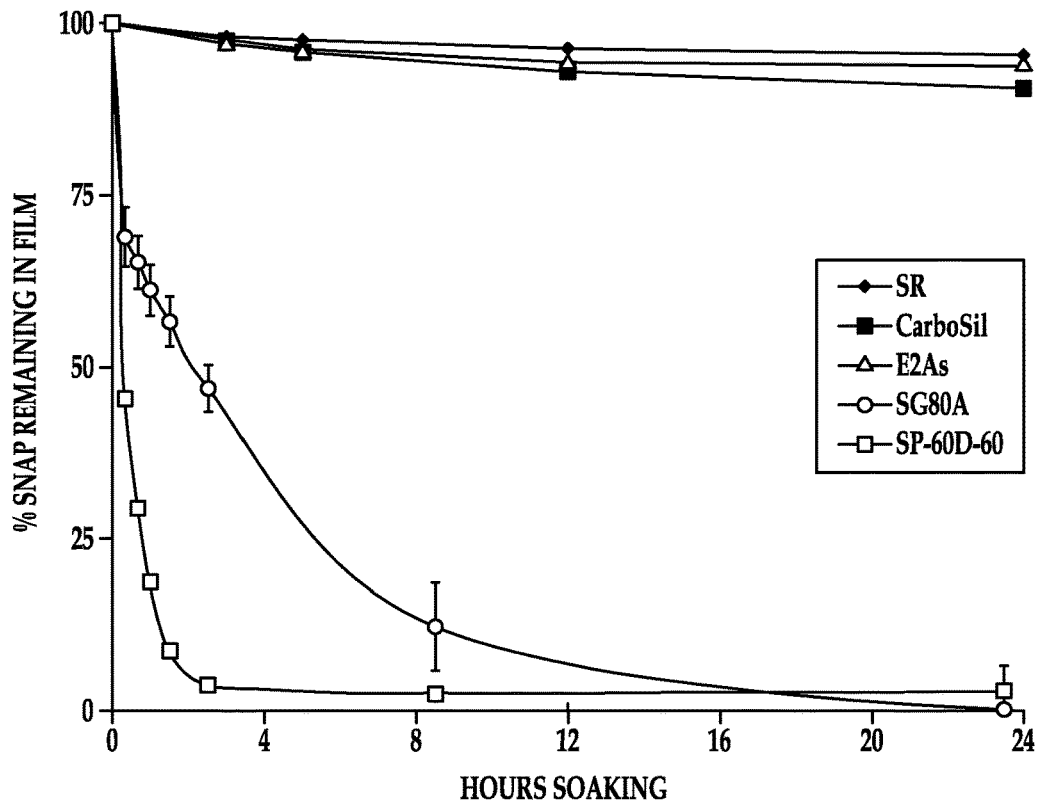

The 5 wt % and 10 wt % SNAP/polymer films were immersed in 4 mL PBS in the dark at room temperature (i.e., 22° C.) or at 37° C. The diffusion of SNAP into the PBS from the various polymer films containing 5 wt % and 10 wt % SNAP was monitored using UV-Vis absorption. As shown in FIGS. 3A and 3B, all of the SNAP diffused out of the SG80A and SP-60D-60 polymer films during the first day of soaking in PBS at room temperature (see FIG. 3A) and at 37° C. (see FIG. 3B). The SP-60D-60 polymer is hydrophilic with a water uptake of about 60 wt %, while the SG80A is more hydrophobic, having a water uptake of about 6 wt % (see Table 2 below).

Table 2 illustrates the water uptake of the 5 biomedical polymers used in the present disclosure. Polymer films (200 mg polymer) were cast in Teflon® ring (d=2.5 cm) on Teflon® plates. Small disks (d=0.7 cm) were cut from the parent films, weighed, and immersed in PBS for 48 hours at 37° C. The wet films were wiped dry and weighed again. The water uptake of the polymer films is reported in Table 2 in weight percent as follows: water uptake (wt %)=($W_{wet}$−$W_{dry}$)/$W_{dry}$×100, where $W_{wet}$ and $W_{dry}$ are the weights of the wet and dry films, respectively.

TABLE 2

| Polymer | Water uptake [wt %] |
|---|---|
| Silicone Rubber | 1.2 ± 0.3 |
| CarboSil | 1.5 ± 0.3 |
| Elast-Eon™ E2As | 1.2 ± 0.1 |
| Tecoflex SG80A | 6.2 ± 0.7 |
| Tecophilic SP-60D-60 | 64.5 ± 0.1 |

As shown in FIGS. 3A and 3B, all of the SNAP leaves the more hydrophilic SP-60D-60 polymer during the initial 2 hours of soaking, while the more hydrophobic SG80A leaches all of the SNAP after 24 hours. Due to the rapid loss of the SNAP from the SP-60D-60 and SG80A polymers, a very large initial burst of NO was observed via chemiluminescence (with a Nitric Oxide Analyzer (NOA)) during the first day of soaking (Day 0), and the films exhibited no SNAP/NO release after one day (data not shown). Therefore, these two polymers provide a quick burst of NO/SNAP and were found not to be suitable for longer-term release of NO/SNAP.

In contrast, the silicone rubber, CarboSil®, and E2As polymers exhibit significantly lower amounts of SNAP diffusing into the soaking buffer after one day (see FIGS. 3A and 3B). For all three of these polymers, an initial burst of SNAP leaching was observed during the first day of soaking, corresponding to rapid water uptake by the polymer. This initial burst was about 10% of the total SNAP molecules incorporated into the films. Small amounts of SNAP continued to leach from these polymers during the subsequent days of soaking Silicone rubber, CarboSil® (a thermoplastic silicone-polycarbonate-urethane), and E2As (a siloxane-base polyurethane elastomer) all are hydrophobic polymers due to their high PDMS content and also have the lowest water uptake (see Table 1 above). SNAP is slightly hydrophobic. Therefore, SNAP should have a preference for remaining in these more hydrophobic polymer films. In addition, it is believed that the hydrophobic property of these polymers also plays a significant role in limiting the diffusion of SNAP into the buffer, due, at least in part, to the minimal water uptake of these polymers.

Figure 4A:
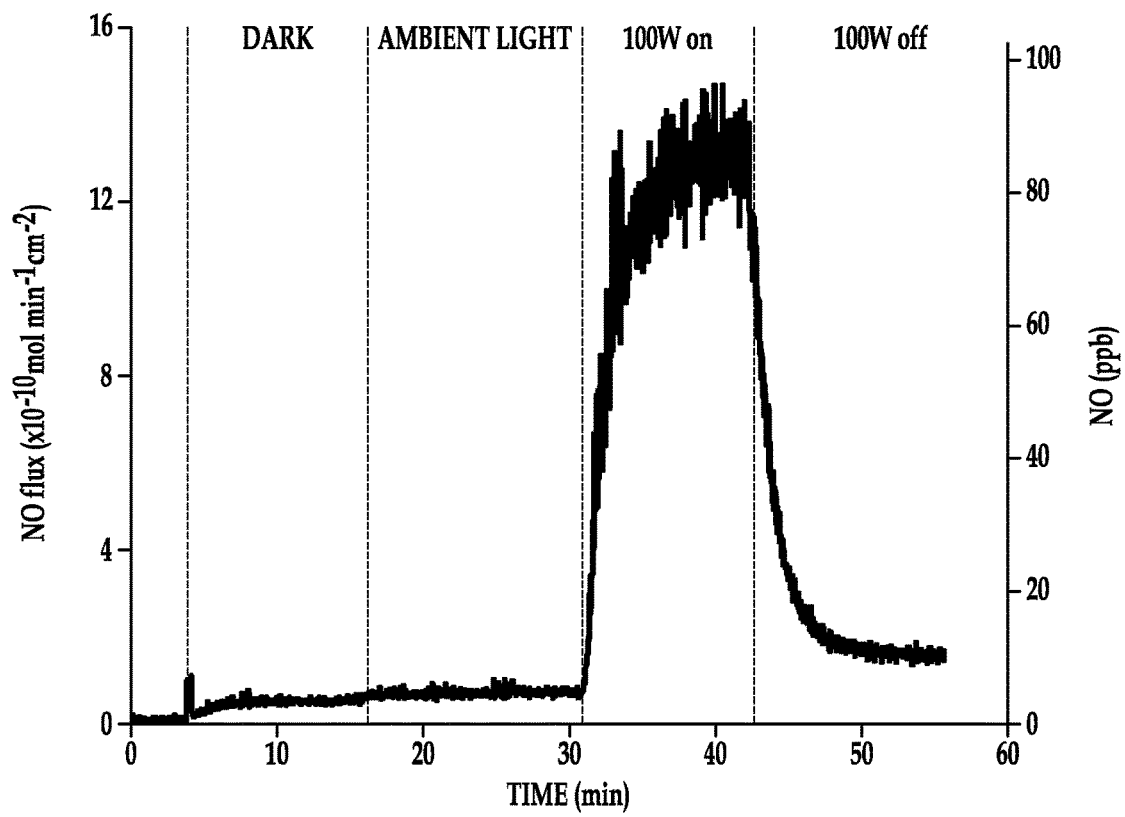
FIG. 4A shows NO release behavior of 10 wt % SNAP/E2As film at 37° C. in the dark, ambient light, and 100 W floodlight (the data is the mean±SEM (n=3))
Figure 4B:
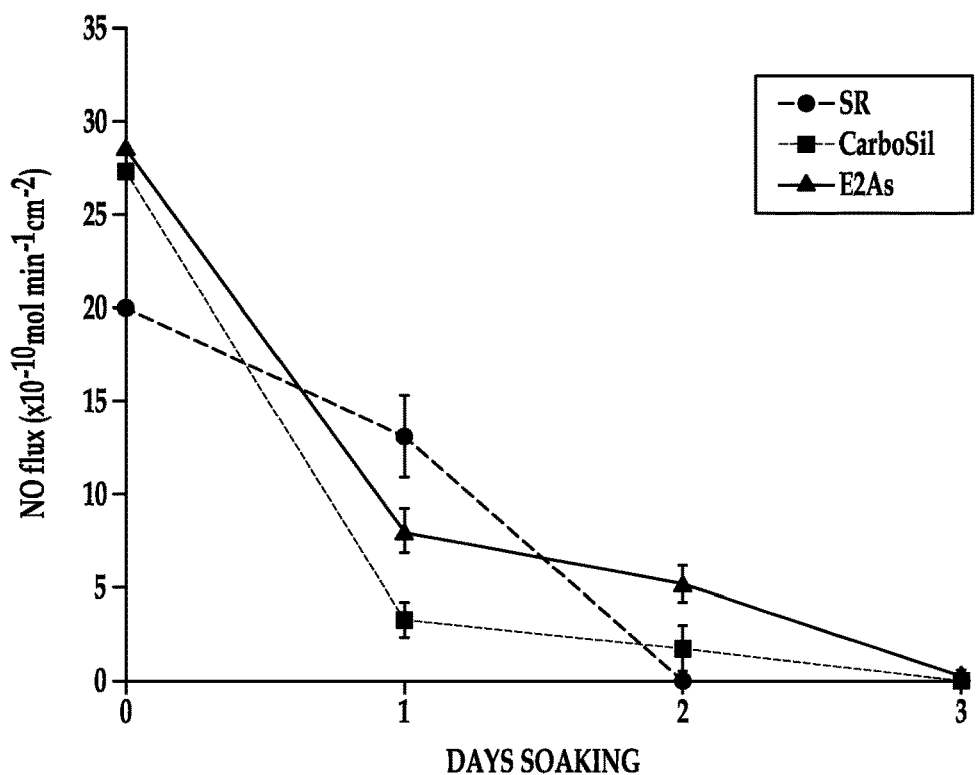
FIG. 4B shows NO release from 10 wt % SNAP in silicone rubber (SR), CarboSil, and Elast-Eon™ E2As films at 37° C. and continuously irradiated with the 100 W floodlight (the data is the mean±SEM (n=3))

The thermal and photoinitiated NO release from the three SNAP-doped polymers (i.e., silicone rubber, CarboSil®, and E2As polymers) was also studied by NOA measurements. Nitric oxide release can be turned on/off using the 100 W floodlight for all 3 film types. FIG. 4A illustrates the NO release behavior of the 10 wt % SNAP/E2As film at 37° C. in the dark, in the ambient light, and in the 100 W floodlight. As shown in FIG. 4A, there is little difference in the NO release from the 10 wt % SNAP/E2As film in the dark or under the ambient lab lights, since ambient fluorescent lighting does not emit the wavelengths responsible for decomposing RSNOs (340 nm or 590 nm). While the data for the 10 wt % SNAP/E2As film is shown, it is to be understood that for all three polymers, the total NO release detected by the NOA for films continuously irradiated with the 100 W floodlight was about 100% of the SNAP doped into the films. The photoinitiated NO release from these three films was examined by continuously irradiating with a 100 W floodlight at 37° C. and monitoring the NO released with the NOA (see FIG. 4B). The SNAP-doped E2As and CarboSil® films exhibited a gradual decrease in the photo-induced NO flux over a 3 day period, while the SR-based films released NO for only 2 days under the same conditions. All three types of films incubated at 37° C. under ambient light yielded an initial burst of NO on the first day of soaking, corresponding to release of SNAP into the solution, and on subsequent days, the NO flux ranged from $1\times10^{-10}$ mol cm$^{-2}$ min$^{-1}$ to $2\times10^{-10}$ mol cm$^2$ min$^{-1}$. This NO flux is still potentially useful to inhibit platelet function and kill bacteria.

Figure 4C:
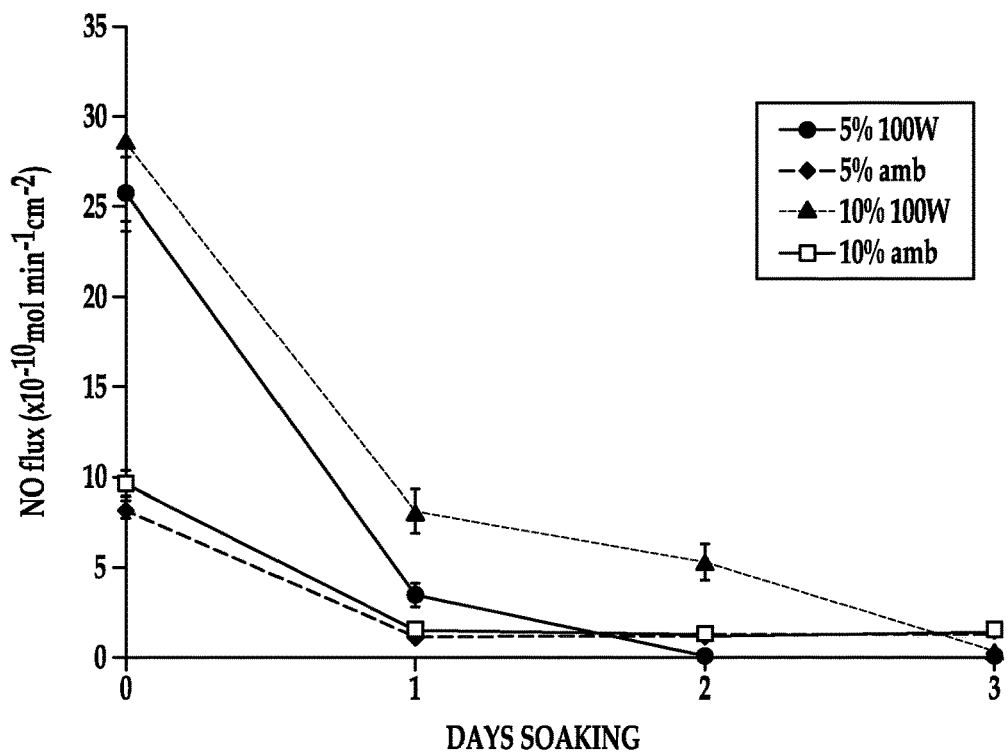
FIG. 4C shows NO release from 5 wt % and 10 wt % SNAP in Elast-Eon™ E2As films at 37° C. continuously under ambient light (amb) or the 100 W floodlight (the data is the mean±SEM (n=3))

It appears that the NO release may be more promising from the film composed of 10 wt % SNAP in E2As under the 100 W floodlight. Therefore, the wt % of SNAP in E2As was varied to 5 wt % and examined in more detail (see FIG. 4C). The NO release and SNAP leaching pattern is similar for the 5 wt % SNAP/E2As film, but the NO release takes place over a shorter time period. The biostability and biocompatibility of the Elast-Eon™ polymers in combination with the NO release from SNAP makes this formulation attractive for further in vitro and possible biomedical applications.

Long-Term NO Release of SNAP/E2As Formulation

Figure 5A:
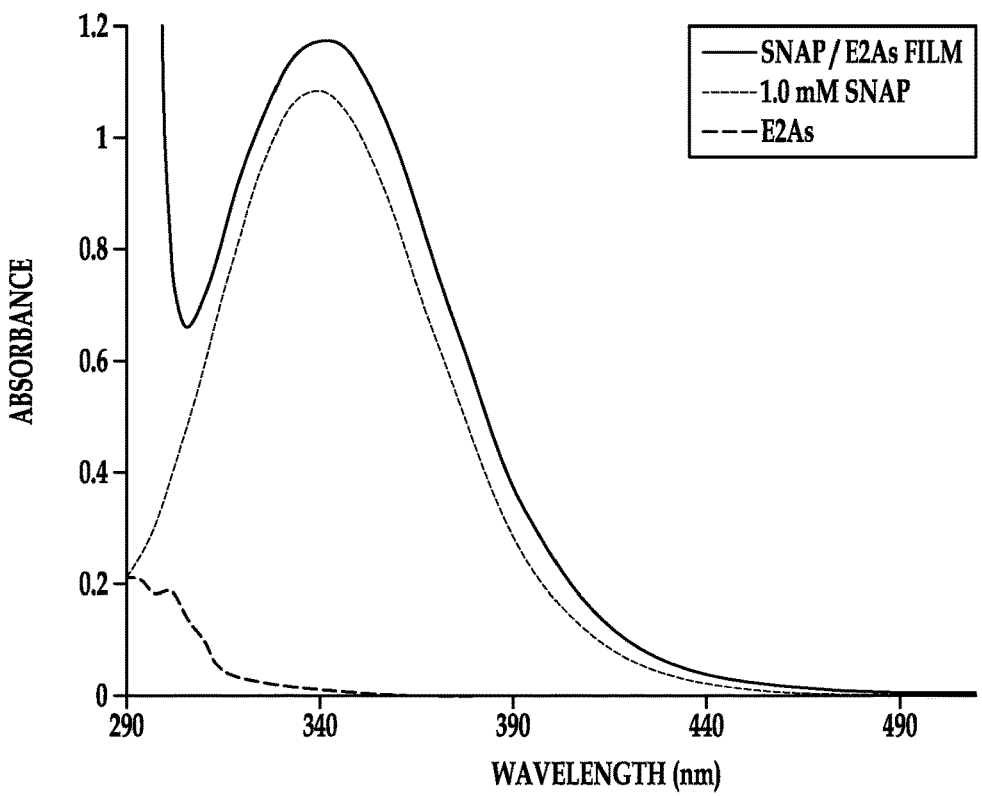
FIG. 5A shows UV-vis spectra of a 10 wt % SNAP/E2As film, 1.0 mM SNAP, and E2As dissolved in N,N-dimethylacetamide (DMAc) (the data is the mean±SEM (n=3))

In vitro studies were conducted with the SNAP/E2As films to examine the long-term NO release and SNAP leaching from these films. The NO release from the SNAP/E2As films over time was determined based on the amount of SNAP decomposed within the polymer phase (i.e., by measuring the SNAP remaining after dissolving the films at given time points). The initial concentration of SNAP in the 10 wt % films was 420 nmol SNAP/mg film. FIG. 5A shows the UV-Vis spectra of 1.0 mM SNAP solution, a 10 wt % SNAP in E2As film redissolved in N,N-dimethylacetamide (DMAc), and E2As dissolved in DMAc.

Figure 5B:
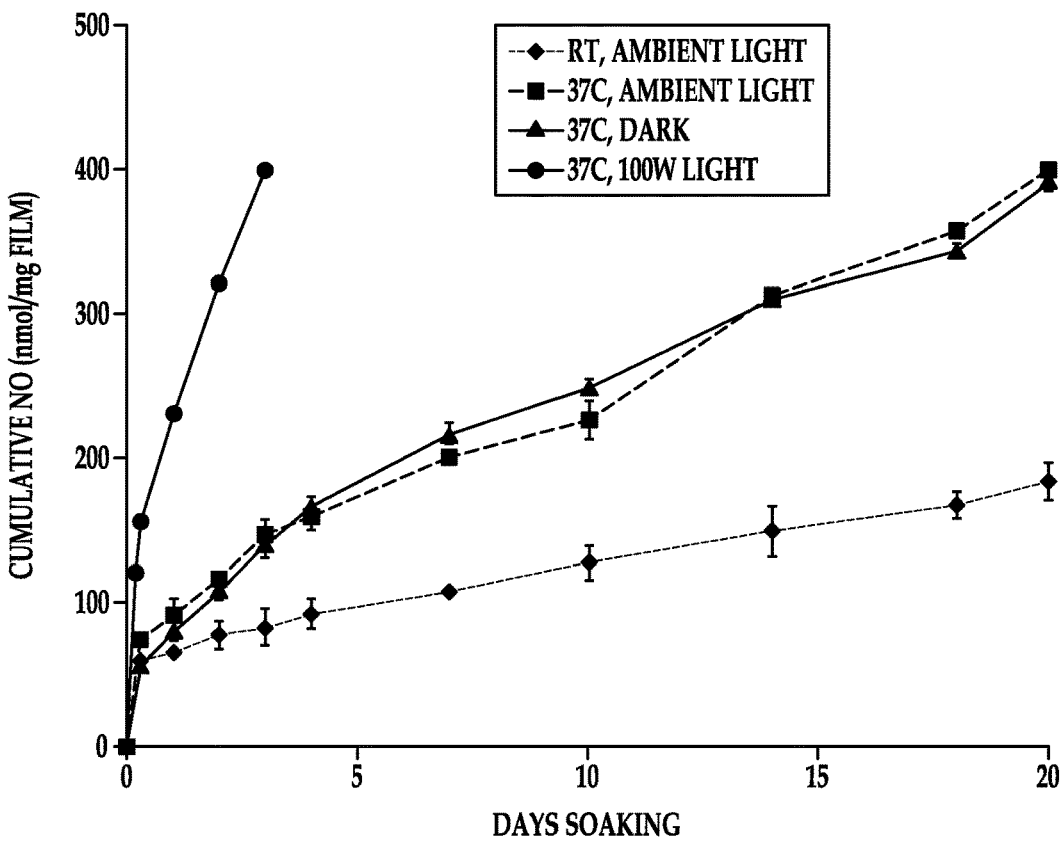
FIG. 5B shows cumulative NO release from 10 wt % SNAP/E2As films incubated in PBS under various conditions: room temperature (22° C.) with ambient light, 37° C. in the dark, 37° C. under ambient light, and 37° C. under the 100 W floodlight (the data is the mean±SEM (n=3))

Due to thermal and/or photochemical decomposition of SNAP, a decrease in the 340 nm absorbance band was observed as the 10 wt % SNAP/E2As films were soaked in PBS under various conditions, and the cumulative NO release based on that absorbance decrease is shown in FIG. 5B. The 10 wt % SNAP/E2As films displayed an initial burst of NO during the first day of soaking (see FIGS. 3A and 3B), which corresponds to the thermal decomposition as well as diffusion of SNAP out of the film. Films soaked at room temperature had the lowest flux of NO release. However, films incubated at 37° C. in the dark or under ambient light exhibited a higher NO release than the films at room temperature. This is due to the increased thermal decomposition of SNAP. The films that were exposed to ambient light yield essentially the same NO release profiles as the films that were soaked in the dark. Nitric oxide release from the SNAP/E2As films that are continuously irradiated with the 100 W floodlight at 37° C. only release NO for 3 days due to their higher NO fluxes that rapidly deplete the SNAP reservoir. These films provide NO release via both a thermal and photoinitiated decomposition of SNAP.

Figure 6A:
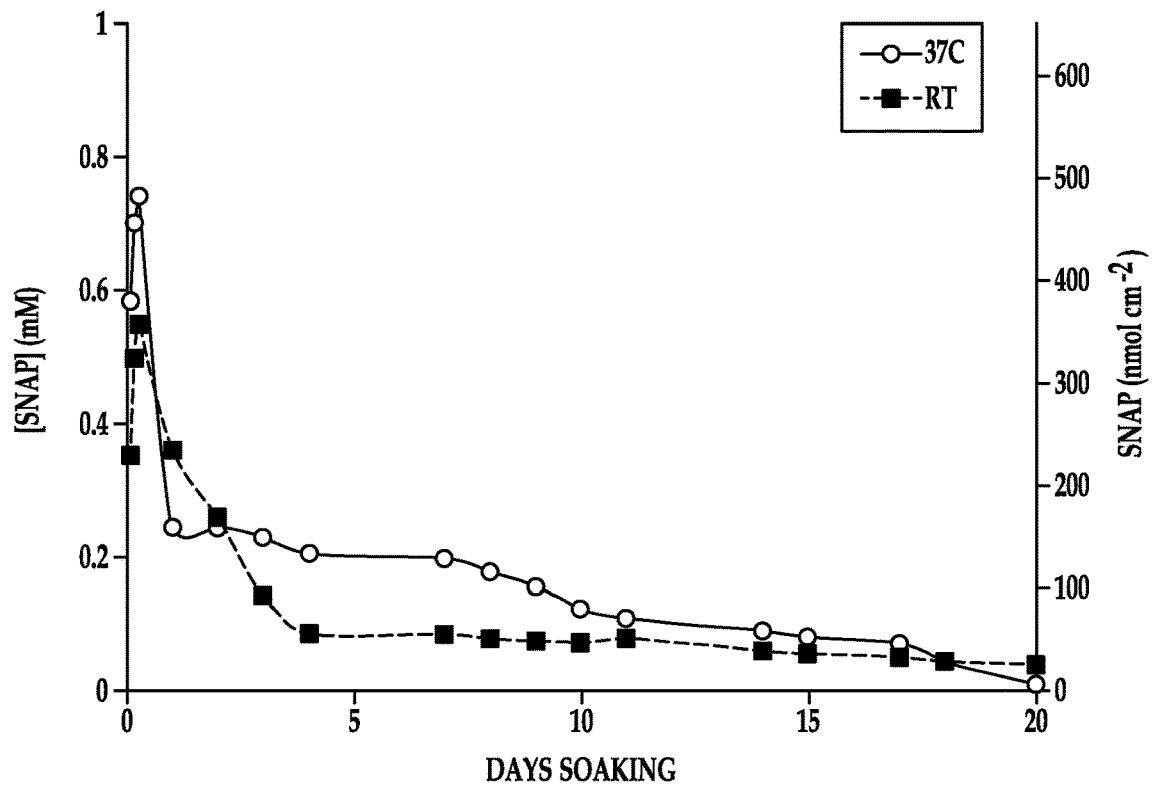
FIG. 6A shows diffusion of SNAP from 10 wt % SNAP-doped E2As films soaking in 1 mL PBS in the dark, as monitored at 340 nm, at room temperature (RT, 22° C.) or 37° C.
Figure 6B:
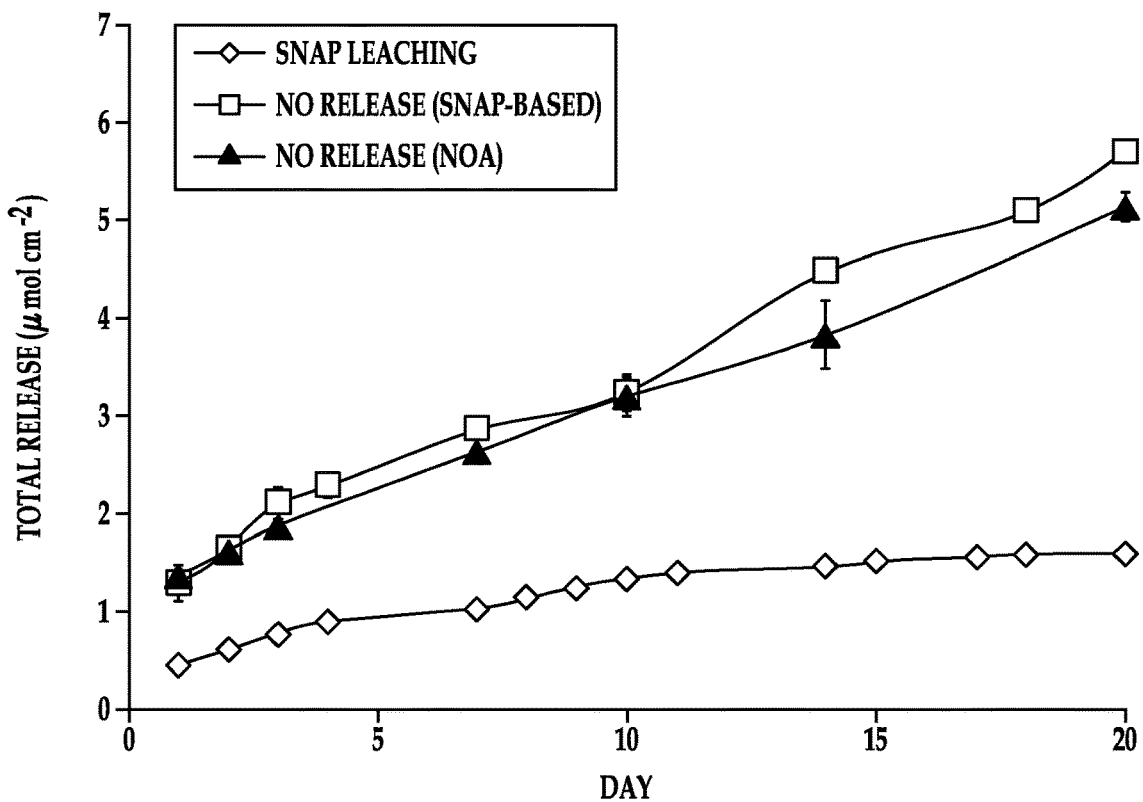
FIG. 6B shows a comparison of the cumulative SNAP leaching and cumulative NO release (from NOA-based or SNAP-based NO release data) from the 10 wt % SNAP-doped E2As films soaking in PBS at 37° C. in the dark. Nitric oxide release from SNAP-doped E2As films can occur from thermal and/or photochemical decomposition of SNAP within the polymer phase, or from SNAP that leached into the aqueous phase. For the SNAP-doped E2As films, approximately 26% of the total NO release is attributed to the SNAP leaching.

Nitric oxide release from the SNAP-doped E2As can occur from thermal and/or photochemical decomposition of SNAP either within the polymer phase, or after SNAP enters the aqueous phase by diffusion out of the polymer. In order to better understand the NO release mechanism of the SNAP/E2As coating, the SNAP diffusion into PBS was monitored over a 20 day period. As shown in FIG. 6A, the films containing 10 wt % SNAP at 37° C. exhibit an initial burst of SNAP leaching on the first day. After this initial burst, the SNAP continues to slowly diffuse from the E2As until the SNAP reservoir is nearly depleted (with still measurable amounts of SNAP leaching on day 20). The total moles of SNAP that leach from the film accounts for about 27% of the total NO released (as detected by NOA measurements) during the 20 day period (see FIG. 6B).

Figure 7:
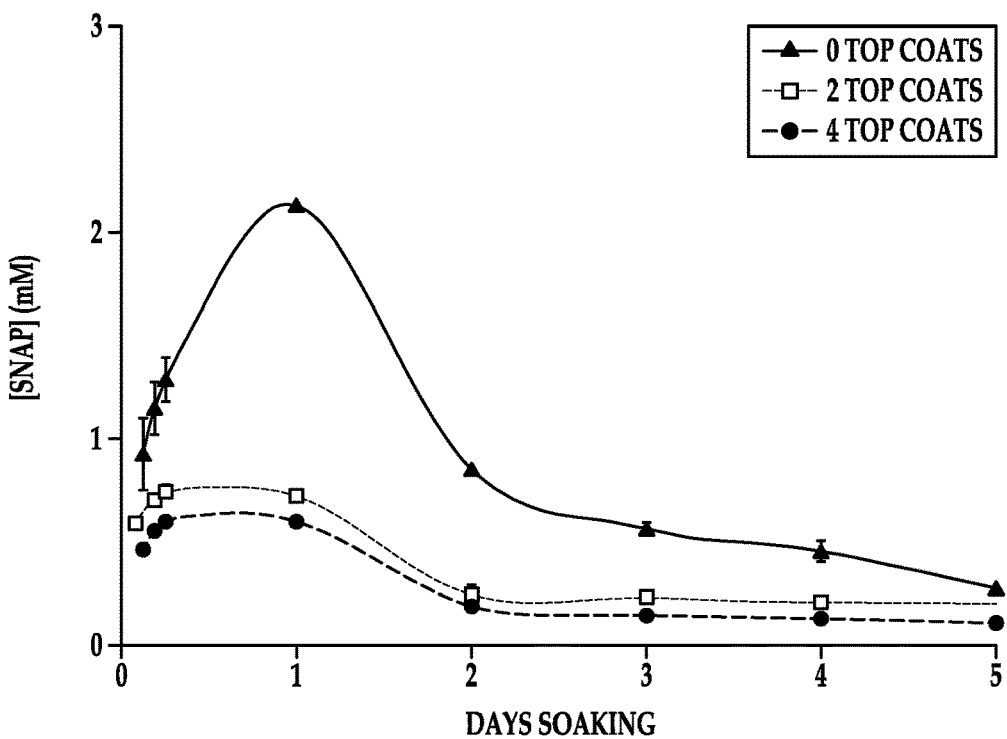
FIG. 7 is a graph showing diffusion of SNAP from 10 wt % SNAP in E2As films with 0, 2, or 4 top coats of E2As as monitored at 340 nm by UV-vis, the films were soaked in 10 mM PBS containing 100 µM EDTA, which was replaced daily after the UV-vis measurement, at 37° C. in the dark (the data is the mean±SEM (n=3))

Additionally, the effect of the number of polymer top coats on loss of SNAP was also evaluated. SNAP-doped E2As films without any top coat exhibit higher levels of SNAP diffusion into the buffer than films with at least 2 topcoats (see FIG. 7). The thickness of the top coat allows control of the diffusion rate of SNAP from the polymer reservoir. As such, in the examples disclosed herein the SNAP-doped films may be coated with a polymer top coat. Examples of suitable polymers for the top coat include the siloxane-based polyurethane elastomers, poly(vinyl chloride), crosslinked polyurethanes, crosslinked silicone rubber, polytetrafluoroethylene, etc. (without the NO donor therein). In some examples, the polymer used for the top coat is the same polymer used for the underlying film.

Stability Study of the SNAP/E2As Films

Figure 8:
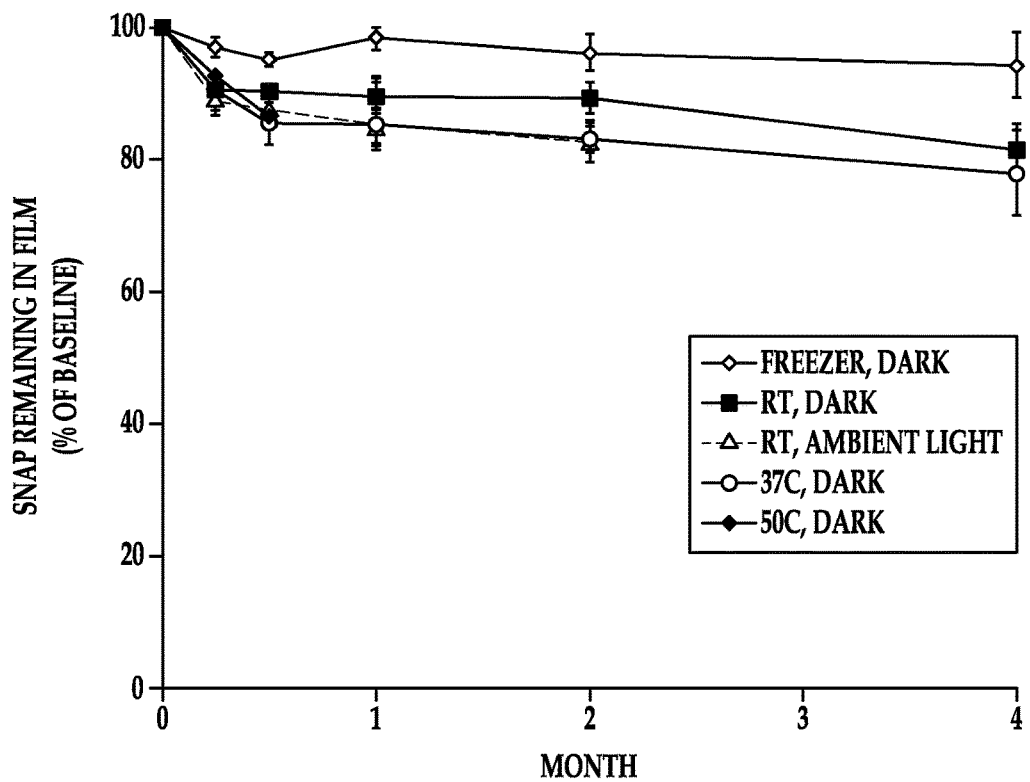
FIG. 8 is a graph showing stability of 10 wt % SNAP in E2As films stored dry with desiccant under various temperature and light conditions, the films were dissolved in DMAc to determine the amount of SNAP remaining at various times (compared to the initial level) as monitored at 340 nm by UV-vis (the data is the mean±SEM (n=3))

The stability of SNAP doped in the E2As polymer during dry storage was also evaluated. SNAP incorporated in E2As can potentially undergo thermal or photochemical decomposition during storage, thus limiting the available NO release capacity at the time of use. Therefore, 10 wt % SNAP/E2As films were stored with desiccant in the freezer in the dark, dry in the dark or in ambient light with desiccant at room temperature, and dry in the dark with desiccant at 37° C. and 50° C. These stability studies were conducted in a similar manner as the cumulative NO release experiments, where films were dissolved in DMAc to determine the amount of SNAP remaining in the polymer at various time points (as described herein). The results indicate that SNAP is stable within the E2As polymer matrix after 4 months. After 2 months, for example, the 10 wt % SNAP films stored in the freezer (−20° C.) in the dark maintain about 96% of the initial SNAP species, compared to 89% for films stored at room temperature and 82% for films stored at 37° C. (see FIG. 8). The results shown in FIG. 8 illustrate the enhanced stability of SNAP during storage. Tertiary RSNOs, such as SNAP, have greater stability than primary RSNOs due to steric hindrance surrounding the sulfur atom. The increased thermal stability of SNAP in combination with the stabilization effect of the E2As polymer provides excellent storage stability of the SNAP/E2As material.

Stability of RSNOs has been studied for viscous polymer matrices containing such NO donors, including poly(ethylene glycol), Pluronic® F127 hydrogel, poly(vinyl alcohol) and poly(vinyl pyrroloidone). RSNOs decompose according to the following sequence of reactions:

$$RSNO \rightarrow RS. + NO. \tag{1}$$

$$RS. + RSNO \rightarrow RSSR + NO. \tag{2}$$

With the overall reaction: $2RSNO \rightarrow RSSR + 2NO$. (3).

The viscosity of the polymer matrix provides a cage effect on the bond cleavage and radical pair recombination. In addition, a viscous polymer matrix also limits the diffusion of the radical species, favoring geminate recombination to reform RSNO. Thus, the E2As polymer not only limits the diffusion of SNAP into the PBS, but it also appears to provide an additional stabilization effect to reduce the rate of SNAP decomposition.

Figure 9:
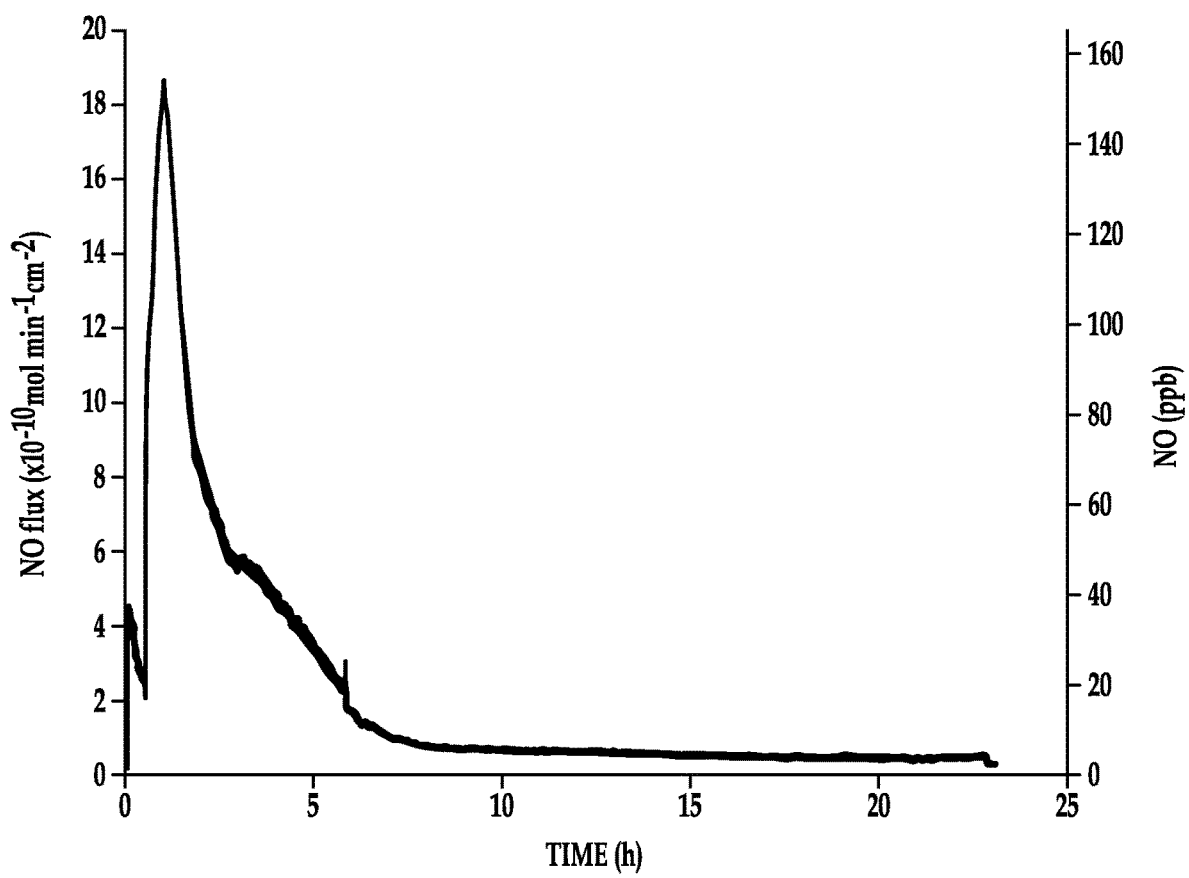
FIG. 9 is a graph showing NO release behavior from 10 wt % SNAP/E2As dry film at 37° C. in the dark.

An experiment was performed to test the storage stability of SNAP in the E2A matrix. FIG. 9 illustrates the results. In particular, FIG. 9 shows NO release behavior from 10 wt % SNAP in E2As dry film at 37° C. in the dark (n=1). The film was dried at 37° C. and then stored at 37° C. Approximately 5% of the total NO in the film was released during the first hours of storage, followed by very low levels of NO release. This corresponds with other storage/stability data disclosed herein (see FIG. 8), which shows that the SNAP loses its NO slowly during the 37° C., dry storage (losing only 10-15% of the SNAP after two months of storage in a dry state).

SNAP/E2As Coated ECC Loops and Effects on Rabbit Hemodynamics

Figure 10:
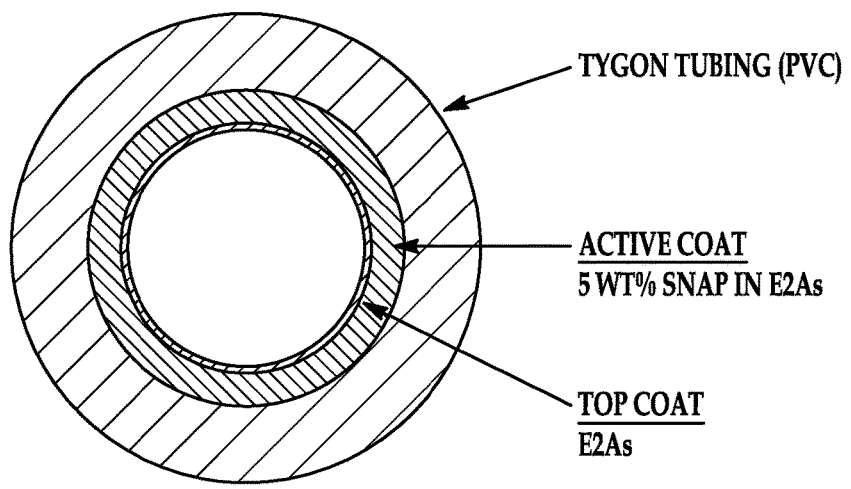
FIG. 10 is a schematic diagram of the extracorporeal circuit (ECC) tubing coated with 5 wt % SNAP/E2As followed by a top coat of E2As.
Figure 11A:
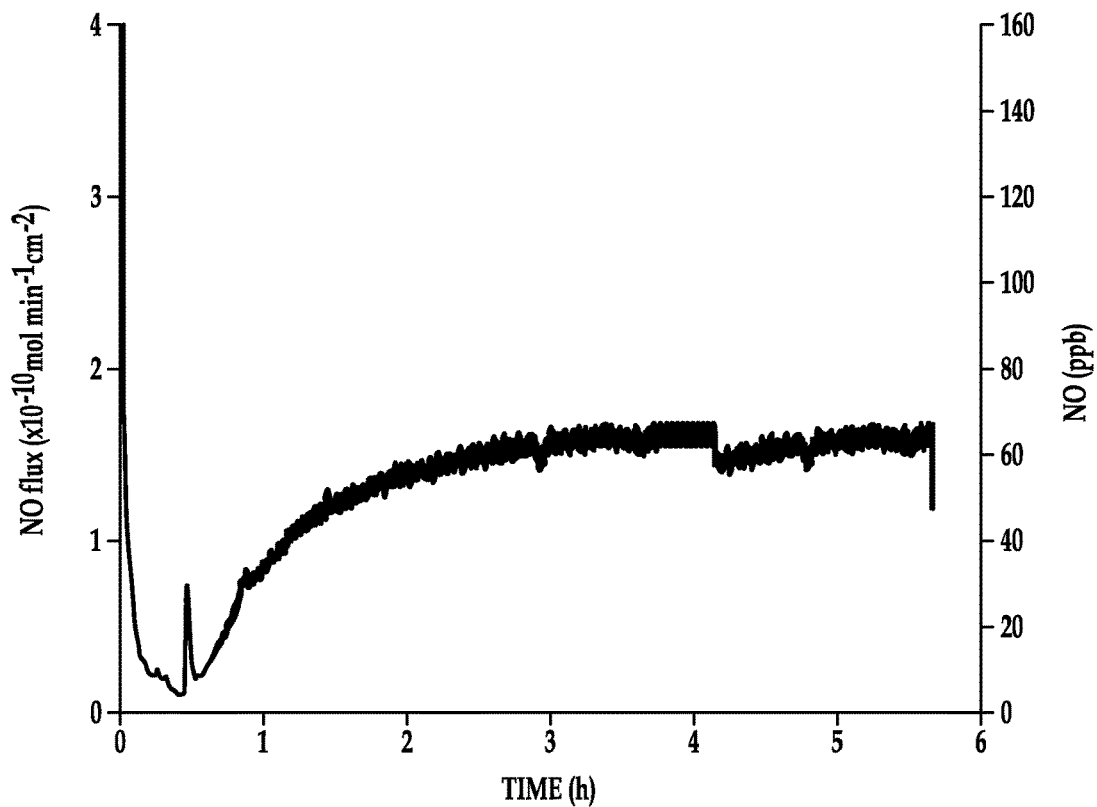
FIGS. 11A and 11B are graphs showing representative NO surface flux profiles from a section of ECC tubing coated with 5 wt % SNAP in E2As before (FIG. 11A) and after (FIG. 11B) blood exposure, NO release was measured via chemiluminescence at 37° C. under ambient light.
Figure 11B:
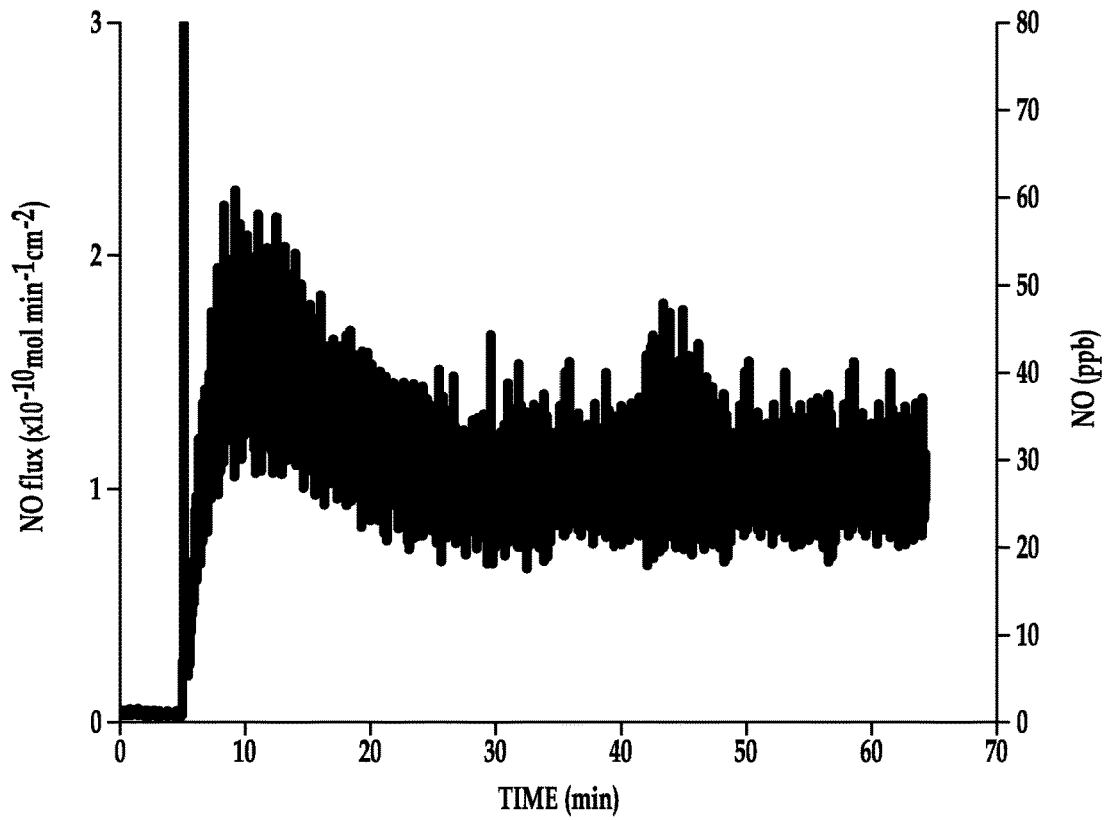

The active ECC loops coated with 5 wt % SNAP in E2As and a top coat of E2As (a schematic cross-section of which is shown in FIG. 10) and control loops coated with E2As only were prepared. 5 wt % SNAP was used in these tests due, in part, to the short duration of the ECC experiment. As described above, the SNAP/E2As coating has an initial burst of SNAP diffusing into solution during the first day of soaking To reduce the effects of this burst during the short-term ECC experiments, all loops were first soaked overnight in saline, and the soaking solution was discarded prior to the ECC experiments. Nitric oxide released from samples of the coated ECC loops were measured with the NOA for NO release before blood exposure (after overnight soaking in saline). The NO release of the SNAP/E2As coated loops maintains an average flux of about $2\times10^{-10}$ mol $cm^{-2}$ $min^{-1}$ for 4 hours (at 37° C. with ambient light) (see FIG. 11A). After 4 hours of exposure to flowing blood, the ECC loops still exhibit a NO flux of at least $1.5\times10^{-10}$ mol $cm^2$ $min^{-1}$ for at an additional 1 hour period (see FIG. 11B).

The hemodynamic effects of the SNAP/E2As coated ECC circuits were also monitored over the 4 hours of blood exposure in the rabbit ECC model. The mean arterial pressure (MAP) dropped significantly for both SNAP/E2As and control loops within the first hour, dropping to 35±2 mmHg and 46±2 mmHg, respectively. The MAP was maintained at these levels for the 4 hours by continuous IV fluid maintenance. The ECC blood flow dropped and remained at 64±5 mL/min for SNAP/E2As ECC, but maintained at baseline levels over the 4 hours (76±6 mL/min) for controls. The MAP drop and slower blood flow for the SNAP/E2As circuits is likely due to the vasodilatory effects of SNAP diffusing from the coating into the blood. The heart rate was maintained over the 4 hours and no significant difference was noted between the SNAP/E2As and control ECC loops, averaging 205±2 beats/min. The activated clotting time increased over the 4 hour period for both SNAP/E2As and control circuits, likely due to the increase in intravascular fluids (the hemodilution effect). Similar effects on MAP and flow rate have been observed with SNAP infusion.

Figure 12A:
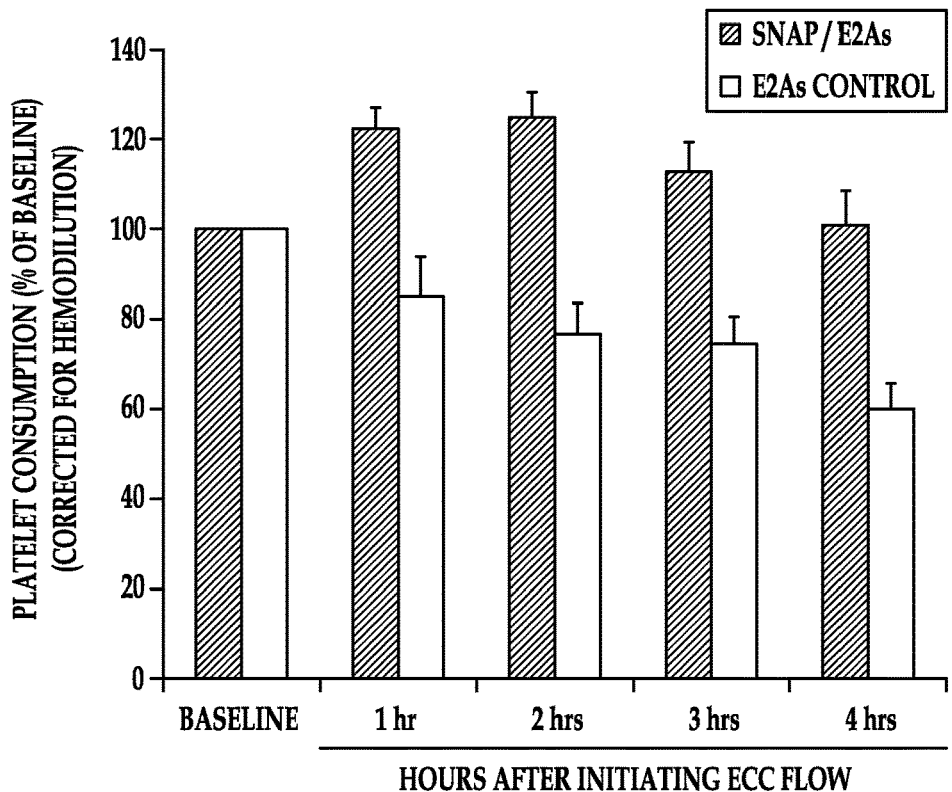
FIGS. 12A and 12B are graphs showing time-dependent effects of the 5 wt % SNAP/E2As coating on platelet count (e.g., consumption) (FIG. 12A) and plasma fibrinogen levels (FIG. 12B) during the 4 hour blood exposure in the rabbit thrombogenicity model (the data is the mean±SEM (n=4))

Effects of SNAP/E2As Coatings on Rabbit Platelet Function and Thrombus Formation Platelet activation and function throughout the 4 hour ECC was assessed by recording the platelet count (e.g., consumption, see FIG. 12A) and plasma fibrinogen levels (see FIG. 12B), which were both corrected for hemodilution due to the added IV fluids, as well as % platelet aggregation. The baseline platelet counts ($\times10^8$ platelets/mL) were 3.5±0.6 and 4.8±0.5 for the 5 wt % SNAP/E2As and E2As control circuits, respectively. For the SNAP/E2As circuits, the platelet count initially rose slightly and was maintained at 100±7% of baseline levels at the end of 4 hours on ECC. The platelet count for control circuits exhibited a time-dependent loss in platelets, dropping to 60±6% of baseline after 4 hours. The percent of platelet functional aggregation was determined by ex vivo collagen stimulation of PRP and measured by optical turbidity. The platelets from blood taken from circulation through the SNAP/E2As and control circuits showed similar response to collagen-stimulated platelet aggregation during the 4 hour blood exposure, both maintaining 56±12% (with baseline values at 68±6%).

Figure 12B:
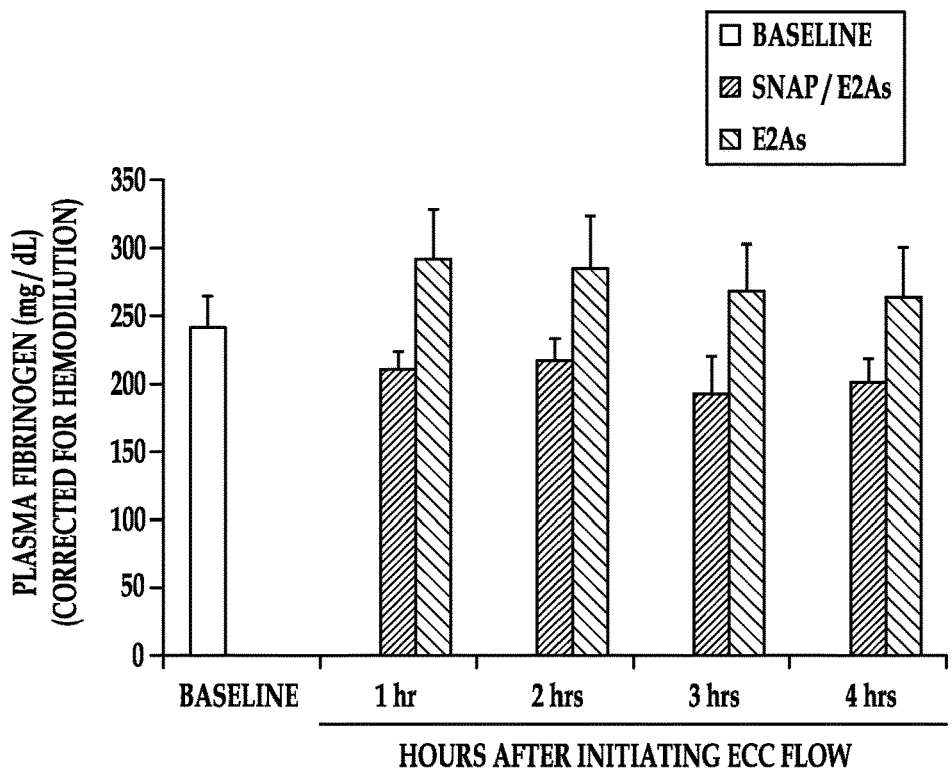
Figure 13:
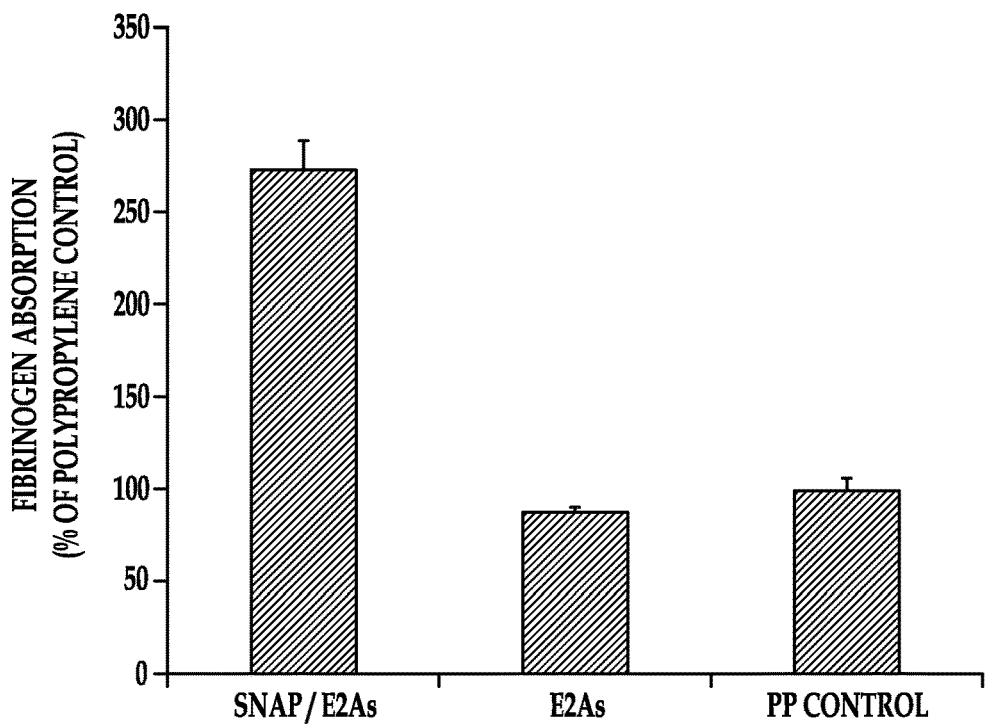
FIG. 13 is a graph showing results of in vitro fibrinogen adsorption assays on the 5 wt % SNAP/E2As and E2As control coatings (fluorescence assay in a 96-well plate that used goat anti-human fibrinogen-FITC conjugated antibody to measure the level of adsorbed human fibrinogen (3 mg/mL) on the coatings, the data is the mean±SEM (n=24))

As shown in FIG. 12B, the plasma fibrinogen levels were maintained at baseline levels for the control circuits. For the 5 wt % SNAP/E2As circuits, the plasma fibrinogen levels during the first hour of ECC dropped to 83% of baseline levels and remained at that level for the 4 hour ECC. This decrease in plasma fibrinogen levels can be attributed to fibrinogen binding to the surfaces, as shown by the in vitro fibrinogen assay results (see FIG. 13). Surprisingly, even with the enhanced adsorption of fibrinogen on the SNAP/E2As coatings, these materials still exhibited significantly less platelet loss than controls, suggesting that the levels of NO produced overcome the enhanced fibrinogen adsorption that would normally enhance activation of platelets.

Figure 14:
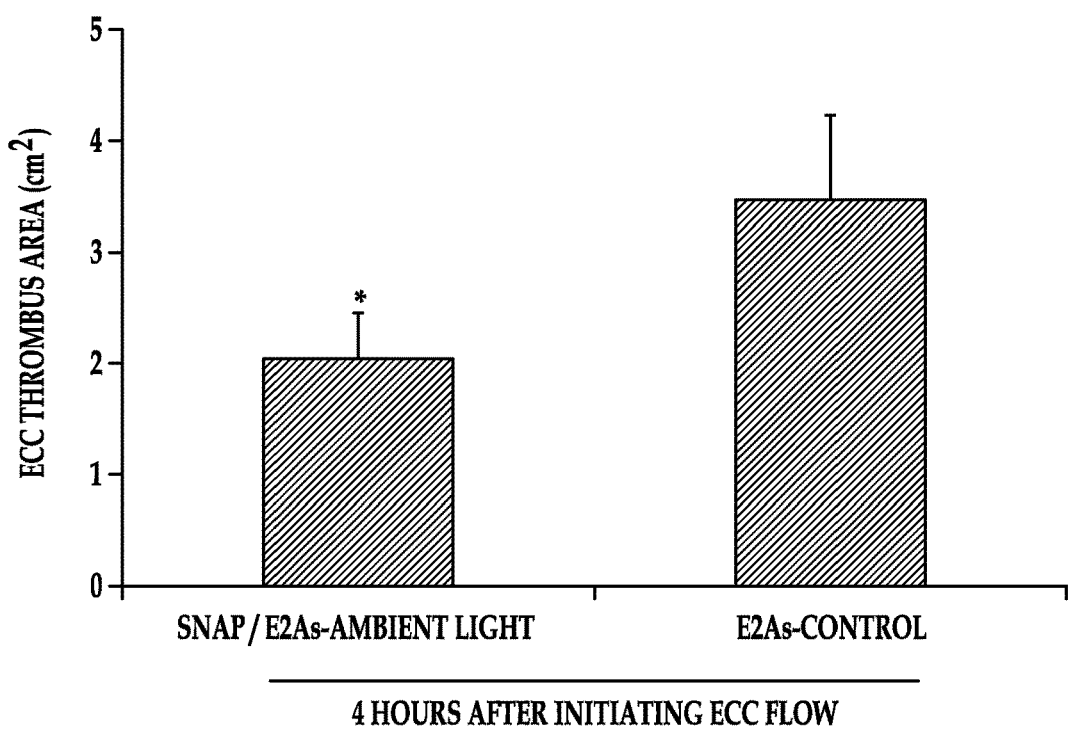
FIG. 14 is a two-dimensional representation of thrombus formation on the SNAP/E2As and control ECCs after 4 hour blood exposure in the rabbit thrombogenicity model, as quantified using ImageJ software from NIH (the data is the mean±SEM (n=4))

To determine the differential formation of thrombus in the thrombogenicity chamber of the ECC circuit (i.e., the ⅜ inch ID Tygon® tubing, 8 cm in length within the ECC loop), 2-dimensional (2D) image analysis was performed after 4 hours of blood exposure. The thrombus area was analyzed by using Image J software and represents the 2D area of thrombus formation (pixels/$cm^2$) in each thrombogenicity chamber. The thrombus area was quantitated and data are shown in FIG. 14. The thrombus area is significantly reduced for the SNAP/E2As circuits when compared to controls, although the E2As controls also had relatively low thrombus area, likely resulting from the enhanced intrinsic biocompatibility of the E2As polymer.

One of the effects of the new SNAP/E2As coating is the hypotension caused by the diffusion of SNAP into the blood stream. The co-administration of intravenous fluids counteracts this, but may in some instances pose difficulties in a clinical situation. Applications of SNAP have been reported to cause hypotension, hyperglycemia and impaired insulin secretion, and decreased cell viability. However, when used as catheters for coatings for small implantable devices, the surface area to volume (of blood) ratios will be quite small, and thus the amounts of SNAP lost to the blood will generally not be a significant issue. Furthermore, endogenous thiols and superoxide dismutase will reduce many of the adverse effects. The parent thiol, N-Acetyl-DL-penicillamine (NAP), however, has been used clinically to treat mercury poisoning and cystinuria with minimal side effects. Although the SNAP/E2As coatings disclosed herein do exhibit a hypotension effect, the daily levels of SNAP delivered by the coating are well below the reported levels causing the other potential adverse side effects described above.

Impregnation Method for Making SNAP-Doped Polymers

The present disclosure further includes a method for loading commercial SR or PU tubing with SNAP. Commercial SR and PU includes medical grade tubing, including those available from US plastics, Cole Palmer, Professional Plastics, ICORally, and Thermedics, Inc. FIG. 15 shows an NO release profile of polyurethane (PU) tubing that was soaked in a SNAP/acetone solution for either 1 or 2 days. The tubing was then rinsed with acetone and dried prior to the NOA testing. The tubing was soaked in PBS at 37° C. for the NOA testing.

This impregnation approach enables the incorporation of the SNAP species within the walls of existing commercial catheters/tubings. This approach avoids problems that may arise when attempting to extrude SNAP into a polymer tubing under normal hot extrusion conditions due to the thermal instability of NO donors (e.g., SNAP and related species) at high temperatures. While acetone was used in the impregnation approach described herein, it is believed that other solvents (or mixtures of solvents) that may be used include ethyl acetate, cyclohexane, isopropanol, methanol, butanone, etc.

SNAP-Doped Polymers for Catheter Tubing Applications

FIG. 16A is a schematic illustration of an E2As catheter tubing prepared with 5 wt % or 10 wt % SNAP/E2As according to an example of the present disclosure followed by the application of a top coat of E2As. FIG. 16B is a cross-section of the catheter tubing, illustrating the various layers. In general, the trilayer catheters were prepared by dip-coating 5 base coats of an E2As solution, 25 coats of the respective active solutions, and 5 top coats of the E2As solution. The SNAP/E2As catheters were kept in phosphate buffered saline (PBS) in the dark at 37° C.

Figure 17:
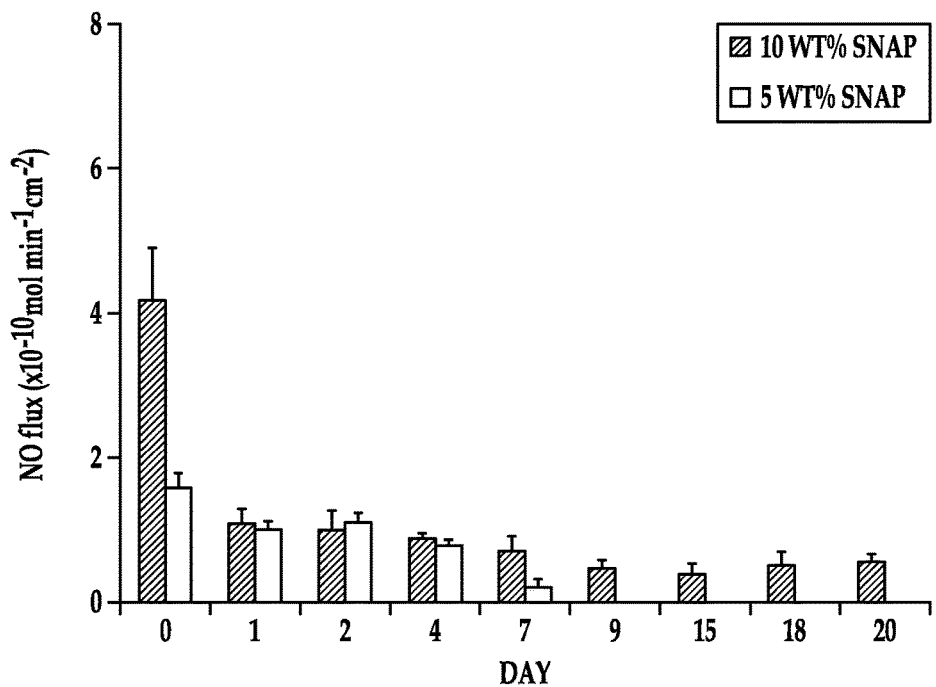
FIG. 17 shows NO release profiles of 5 wt % and 10 wt % SNAP/E2As catheters at 37° C. in the dark (n=5)

FIG. 17 shows 20 day NO release of the SNAP/E2As catheters at 37° C. in the dark in the phosphate buffered saline (PBS). The results in FIG. 17 illustrate that the 10 wt % SNAP/E2As catheters were able to release NO for up to 20 days and that the 5 wt % SNAP/E2As catheters were able to release NO for up to 7 days at the specified conditions.

Figure 18:
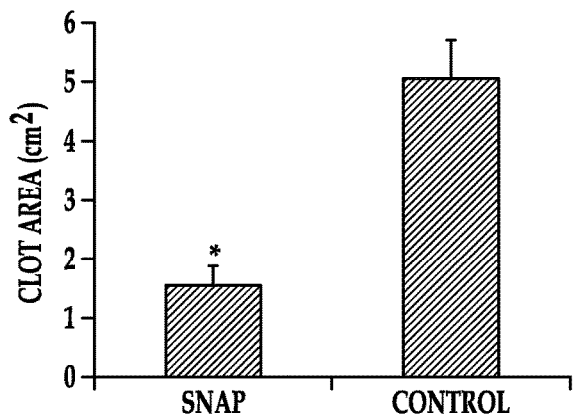
FIG. 18 is a graph showing quantitation of thrombus area on SNAP/E2As catheters and E2As control catheters after 7 day implantation in sheep, as calculated with NIH ImageJ software using a 2D representation of thrombus (the data are means±SEM (n=5)), *=p<0.05.
Figure 19:
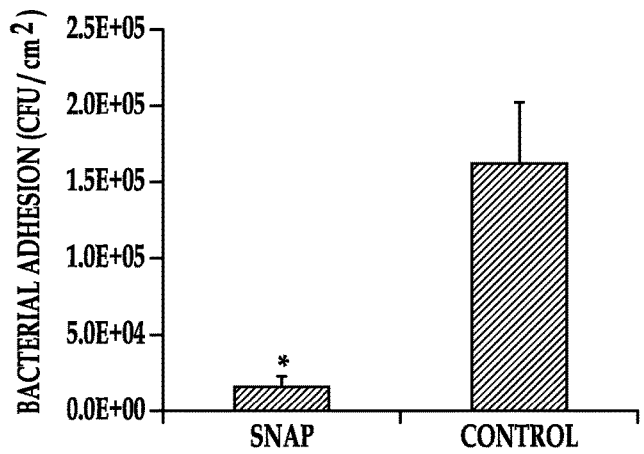
FIG. 19 is a comparison of bacterial adhesion (CFU/cm$^2$) on 1 cm piece of explanted SNAP/E2As catheters and E2As control catheters (the data are means±SEM (n=5)), *=p<0.05.

E2As control catheters and the 10 wt % SNAP/E2As catheters were implanted in sheep veins for 7 days. After explantation, the SNAP/E2As catheters were found to have significantly less thrombus (FIG. 18) and a 90% reduction of bacterial adhesion (FIG. 19) than the E2As control catheters. Together FIGS. 17 through 19 demonstrate the potential application of the SNAP-doped polymers in the catheter configuration.

To further illustrate the present disclosure, various examples are given herein. It is to be understood that these examples are provided for illustrative purposes and are not to be construed as limiting the scope of the present disclosure.

Examples

It is to be understood that the SNAP doped polymers and the data previously described herein were made using the materials and techniques described in the EXAMPLES section. The various testing procedures described in the EXAMPLES section were also used.

Materials

N-Acetyl-DL-penicillamine (NAP), sodium chloride, potassium chloride, sodium phosphate dibasic, potassium phosphate monobasic, ethylenediaminetetraacetic acid (EDTA), tetrahydrofuran (THF), sulfuric acid and N,N-dimethylacetamide (DMAc) were purchased from Sigma-Aldrich (St. Louis, Mo.). Methanol, hydrochloric acid and sulfuric acid were obtained from Fisher Scientific (Pittsburgh, Pa.). Tecophilic™ SP-60D-60 and Tecoflex™ Sg-80A were products of Lubrizol Advanced Materials Inc. (Cleveland, Ohio). Dow Corning RTV 3140 Silicone Rubber (SR) was purchased from Ellsworth Adhesives (Germantown, Wis.). CarboSil® 20 90A was from the Polymer Technology Group (Berkeley, Calif.). Elast-Eon™ E2As was obtained from AorTech International, PLC (Scoresby, Victoria, Australia). Human plasma fibrinogen containing >90% clottable proteins was a product of Calbiochem (La Jolla, Calif.), and fluorescein-labeled goat IgG (polyclonal) against denatured human fibrinogen was purchased from MP Biomedicals, LLC (Solon, Ohio). Black, polypropylene 96-well microtiter plates used for fluorescence measurements were obtained from Nalge Nunc International (Rochester, N.Y.). All aqueous solutions were prepared with 18.2 MΩ deionized water using a Milli-Q filter (Millipore Corp., Billerica, Mass.). Phosphate buffered saline (PBS), pH 7.4, containing 138 mM NaCl, 2.7 mM KCl, 10 mM sodium phosphate, 100 µM EDTA was used for all in vitro experiments.

Synthesis of SNAP

SNAP was synthesized using a modified version of a previously reported method (I. Chipinda, R. H. Simoyi, *Journal of Physical Chemistry B* 2006, 110, 5052). Briefly, an equimolar ratio of NAP and sodium nitrite was added to a 1:1 mixture of water and methanol containing 2 M HCl and 2 M $H_2SO_4$. After 30 minutes of stirring, the reaction vessel was cooled in an ice bath to precipitate the green SNAP crystals. The crystals were collected by filtration, washed with water, and allowed to air dry. The reaction and crystals were protected from light at all times.

Preparation of SNAP-Doped Films

The polymer films containing 5 wt % and 10 wt % SNAP were prepared by solvent evaporation. For the 10 wt % SNAP films, the casting solutions were prepared by dissolving 180 mg of the respective polymer in THF. The polyurethanes (SP-60D-60, SG-80A, CarboSil® and Elast-Eon™ E2As) were dissolved in 3 mL THF, and SR was dissolved in 1 mL THF. SNAP (20 mg) was then added to the polymer solution, and the mixture was stirred for 10 minutes. The 5 wt % SNAP films were prepared similarly with SNAP (10 mg) and polymer (190 mg). The film solution was cast in a Teflon® ring (d=2.5 cm) on a Teflon® plate and dried overnight under ambient conditions. Small disks (d=0.7 cm) were cut from the parent films and were dip coated 2 times with a topcoat solution (200 mg of the respective polymer (no SNAP added) in 4 mL THF) and dried overnight. As such, the topcoat for each sample was made of the same polymer as the parent film. The weight of each small disk was recorded prior to topcoating. All films and film solutions were protected from light. The final films had a SNAP-doped layer that was about 150 µm thick and a top coat that was about 50 µm thick.

Preparation of SNAP/E2As Coated ECC Loops

The ECC configuration employed in the in vivo rabbit study consisted of 16-gauge and 14-gauge IV polyurethane angiocatheters (Kendall Monoject Tyco Healthcare, Mansfield, Mass.), two 16 cm in length ¼ inch inner diameter (ID) Tygon® tubing, and an 8 cm length of ⅜ inch ID Tygon® tubing that created a thrombogenicity chamber where thrombus could form more easily due to more turbulent blood flow.

As previously mentioned, due to the short duration of the ECC experiments (4 hours), the NO release ECC loops were coated with only 5 wt % SNAP in E2As. The SNAP/E2As solution was prepared by dissolving SNAP (125 mg) and E2As (2375 mg) in THF (15 mL). The E2As control solution consisted of E2As in (2500 mg in 15 mL). SNAP/E2As loops were first coated with 2 layers of the SNAP/E2As solution, followed by 1 coat of the E2As control solution. E2As control loops were coated with 2 coats of the E2As control solution. ECC loops were allowed to air dry for 1 hour in the dark between each coat. The completely coated ECC was welded together using THF, starting at the left carotid artery side, with the 16-gauge angiocatheter, one 15 cm length ¼ inch ID tubing, the 8 cm length thrombogenicity chamber, the second 15 cm length ¼ inch ID tubing and finally the 14-gauge angiocatheter. The angiocatheters were interfaced with tubing using two luer-lock PVC connectors. The assembled ECC loops were dried under vacuum while protected from light for at least 48 hours. Prior to the ECC experiment, the loops were filled with saline solution for overnight soaking, and this solution was discarded immediately before the rabbit experiment.

In Vitro Characterization of SNAP-Doped Films

UV-Vis Spectra

All UV-Vis spectra were recorded in the wavelength range of 200 nm-700 nm using a UV-Vis spectrophotometer (Lambda 35, Perkin-Elmer, Mass.) at room temperature. The presence of the S—NO group of SNAP provides characteristic absorbance maxima at 340 nm and 590 nm, corresponding to the $\pi \rightarrow \pi^*$ and $nN \rightarrow \pi^*$ electronic transitions.

Diffusion of SNAP from SNAP-Doped Polymer Films Immersed in PBS

Top coated films were placed in individual vials soaked in 10 mM PBS, pH 7.4, containing 100 μM EDTA to minimize any trace metal ion catalyzed decomposition of SNAP. Films were incubated in the dark at room temperature (22° C.) or 37° C. At various time points, the UV-Vis spectra of a 1 mL aliquot of the PBS was taken for rapid determination of the SNAP concentration. The aliquots were protected from light and were immediately returned to the sample vials for the duration of the experiment. The films were placed in fresh PBS buffer daily. The molar absorption coefficient for SNAP in PBS at 340 nm was determined to be: $\varepsilon_{SNAP}=1024$ $M^{-1}$ $cm^{-1}$.

Cumulative NO Release from SNAP/E2As Films

After the 10 wt % SNAP in E2As films were prepared, the UV-Vis spectra were recorded of individual films dissolved in DMAc to determine the initial concentration of SNAP within the films (nmol SNAP/mg film). Equivalent films were then placed in individual vials containing 3 mL PBS (pH 7.4) containing 100 μM EDTA. Films were incubated under various conditions: RT under ambient light, 37° C. under ambient light, 37° C. in dark, and 37° C. under a 100 W floodlight. The fluorescent lights in the laboratory are referred to as ambient light. Films were placed in fresh PBS daily. At various time points, the films were dissolved in DMAc for rapid determination of the SNAP present in the film. The amount of NO released was determined indirectly from the amount of SNAP decomposed at various time points. The cumulative NO released over time ($[NO]_t$) was calculated by the difference between the initial amount of SNAP in the film ($[SNAP]_0$) and the amount of SNAP at time t ($[SNAP]_t$): $[NO]_t=[SNAP]_0-[SNAP]_t$ (where concentrations are in nmol/mg film). This calculation was based on the fact that the decay of the 340 nm absorption band of SNAP is directly associated with the hemolytic cleavage of the S—NO bond and concomitant NO release. The molar absorption coefficient for SNAP in DMAc at 340 nm was determined to be: $\varepsilon_{SNAP}=1025$ $M^{-1}$ $cm^{-1}$.

NO Release Measurements

Nitric oxide released from the films was measured using a Sievers chemiluminescence Nitric Oxide Analyzer (NOA) 280 (Boulder, Colo.). Films were placed in the sample vessel immersed in PBS (pH 7.4) containing 100 μM EDTA. Nitric oxide was continuously purged from the buffer and swept from the headspace using an $N_2$ sweep gas and bubbler into the chemiluminescence detection chamber. Clear glass sample vessels were used for the ambient light and photoinitiated NO release experiments. A 100 W halogen floodlight (GE model 17986) was placed about 60 cm from the sample cell for the photolysis experiments. Films were incubated in the PBS under the same conditions as the NOA measurements (ambient light or 100 W floodlight irradiation at 37° C.).

SNAP/E2As Stability Study

SNAP/E2As films (consisting of 10 wt % SNAP) were placed under the following conditions in vials with desiccant: room temperature with ambient light, room temperature in dark, 37° C. in dark, and in the freezer (−20° C.) in dark. At various time points over a 4 month period, films were dissolved in DMAc, and the UV-Vis spectra was recorded to determine the % SNAP remaining in the film, as compared to the initial 10 wt % SNAP.

In Vitro Fibrinogen Adsorption Assay

The in vitro fibrinogen adsorption immunofluorescence assay was performed in a 96-well format. The SNAP/E2As and E2As control polymer solutions used to prepare the ECC circuits were also employed to coat microwells of the 96-well microtiter plates and were dried under the same conditions as the ECC loops. Briefly, human fibrinogen was diluted to 3 mg/mL with Dulbecco's phosphate-buffered saline (dPBS) without $CaCl_2$ and $MgCl_2$ (Gibco Invitrogen, Grand Island, N.Y.), equivalent to the human plasma concentration, and then used for adsorption experiments. One hundred μL of this solution were added to each well and the coated wells were incubated with this solution for 1.5 hours at 37° C. This was followed by eight washing steps using wash buffer (100 μL) for each wash, which consisted of a 10-fold dilution of the AbD Serotec Block ACE buffer (Raleigh, N.C.) containing 0.05% Tween 20 (Calbiochem La Jolla, Calif.). To block nonspecific antibody binding, coated wells were incubated with 100 μL of blocking buffer (4-fold dilution of Serotec Block ACE buffer) for 30 minutes at 37° C. After rinsing 3 times with wash buffer (100 μL per well), a background fluorescence measurement of the plates was performed at 485 nm (excitation) and 528 nm (emission) on a Synergy 2 fluorescence microplate reader (Biotek Winooski, Vt.). To detect the adsorbed fibrinogen, fluorescein-labeled goat anti-human fibrinogen antibody was diluted (1:10) in a 10-fold dilution of the Serotec Block ACE buffer and 100 μL of this final solution was added to each well. The antibody was allowed to bind to the surface-adsorbed fibrinogen for 1.5 hours at 37° C. Human fibrinogen adsorption to non-coated polypropylene was used as an internal control to normalize the fluorescence signals within different plates. All measurements were conducted in triplicate.

Rabbit ECC Thrombogenicity Experiments

All animal handling and surgical procedures employed were approved by the University Committee on the Use and Care of Animals in accordance with university and federal regulations. A total of 8 New Zealand white rabbits (Covance, Battle Creek, Mich.) were used in this study. All rabbits (2.5 kg-3.5 kg) were initially anesthetized with intramuscular injections of 5 mg/kg xylazine injectable (AnaSed® Lloyd Laboratories Shenandoah, Iowa) and 30 mg/kg ketamine hydrochloride (Hospira, Inc., Lake Forest, Ill.). Maintenance anesthesia was administered via isoflurane gas inhalation at a rate of 1.5%-3% via mechanical ventilation which was done via a tracheotomy and using an A.D.S. 2000 Ventilator (Engler Engineering Corp. Hialeah, Fla.). Peek inspiratory pressure was set to 15 cm of $H_2O$, and the ventilator flow rate set to 8 L/min. In order to aid in maintenance of blood pressure stability, IV fluids of Lactated Ringer's were given at a rate of 10 mL/kg/h. For monitoring blood pressure and collecting blood samples, the rabbits' right carotid artery were cannulated using a 16-gauge IV angiocatheter (Jelco®, Johnson & Johnson, Cincinnati, Ohio). Blood pressure and derived heart rate were monitored with a Series 7000 Monitor (Marquette Electronics Milwaukee, Wis.). Body temperature was monitored with a rectal probe and maintained at 37° C. using a water-jacketed heating blanket. Prior to placement of the arteriovenous (AV) custom-built extracorporeal circuit (ECC), the rabbit left carotid artery and right external jugular vein were isolated and baseline hemodynamics as well as arterial blood pH, $pCO_2$, $pO_2$, total hemoglobin and methemoglobin were measured using an ABL 825 blood-gas analyzer and an OSM3 Hemoximeter (Radiometer Copenhagen, DK). In addition, baseline blood samples were collected for platelet and total white blood cell (WBC) counts which were measured on a Coulter Counter Z1 (Coulter Electronics Hialeah, Fla.). Plasma fibrinogen levels were determined using a Dade Behring BCS Coagulation Analyzer (Siemens, Deerfield, Ill.), activated clotting times (ACT) were monitored using a Hemochron Blood Coagulation System Model 801 (International Technidyne Corp., Edison, N.J.), and platelet function was assessed using a Chrono-Log optical aggregometer model 490 (Havertown, Pa.).

After baseline blood measurements, the AV custom-built ECC was placed into position by cannulating the left carotid artery for ECC inflow and the right external jugular vein for ECC outflow. The flow through the ECC was initiated by unclamping the arterial and venous sides of ECC, and blood flow in circuit was monitored with an ultrasonic flow probe and flow meter (Transonic HT207, Ithaca, N.Y.). Animals were not systemically anticoagulated during the experiments.

After 4 hours on ECC, the circuits were clamped, removed from animal, rinsed with 60 mL of saline and drained. Any residual thrombus in the larger tubing of ECC (i.e., thrombogenicity chamber) was photographed, and the degree of thrombus was quantitated using Image J imaging software from National Institutes of Health (Bethesda, Md.). Prior to euthanasia, all animals were given a dose of 400 U/kg sodium heparin to prevent necrotic thrombosis. The animals were euthanized using a dose of Fatal Plus (130 mg/kg sodium pentobarbital) (Vortech Pharmaceuticals, Dearborn, Mich.). All animals underwent gross necropsy after being euthanized, including examination of the lungs, heart, liver and spleen for any signs of thromboembolic events.

Blood Sampling

Rabbit whole blood samples were collected in non-anticoagulated 1 cc syringes for ACT, and in 3.2% sodium citrate vacutainers (Becton, Dickinson, Franklin Lakes, N.J.) with 3 cc volumes for cell counts and aggregometry, and 1 cc syringes containing 40 U/mL of sodium heparin (APP Pharmaceuticals, LLC, Schaumburg, Ill.) for blood-gas analysis. Following the initiation of ECC blood flow, blood samples were collected every hour for 4 hours for these in vitro measurements. Samples were used within 2 hours of collection to avoid any activation of platelets, monocytes or plasma fibrinogen.

Platelet Aggregometry

Rabbit platelet aggregation was assayed based on the Born's turbidimetric method using a Chrono-Log optical aggregometer. Briefly, citrated blood (1:10 blood to 3.2% sodium citrate solution) was collected (6 mL), and platelet-rich plasma (PRP) was obtained by centrifugation at 110×g for 15 minutes. Platelet-poor plasma (PPP) was obtained by another centrifugation of the PRP-removed blood sample at 2730×g for 15 minutes and was used as the blank for aggregation.

PRP was incubated for 10 minutes at 37° C. and then 25 µg/mL collagen (Chrono-PAR #385 Havertown, Pa.) was added. The percentage of aggregation was determined 3 minutes after the addition of collagen using Chrono-Log Aggrolink software.

Preparation of SNAP-Doped E2As and E2As Control Catheters

Catheters were prepared by dip-coating polymer solutions on 18 cm long stainless steel mandrels of 2 mm diameter (purchased from McMaster Can). For the E2As control catheters, the polymer solution consisted of E2As dissolved in THF (150 mg/mL). Thirty-five coats of the E2As solution was applied on the mandrel by dip-coating at an interval of 2 min between each coat. For the SNAP/E2As catheters, two different solutions, namely a top/base coat solution and an active solution, were prepared to make the trilayer catheters (see FIG. 16). The top/base coat solution consisted of E2As dissolved in THF (150 mg/mL). The active solution was made up of 10 wt % SNAP and 90 wt % E2As was dissolved in THF with overall concentration of 150 mg/mL. Trilayer catheters were prepared by dip-coating 5 base coats of E2As solution, 25 coats of active solution, and 5 top coats of E2As solution. Catheters used for sheep studies were 15 cm long.

Long-Term (7 Day) Implantation of Catheters in Sheep

Sheep Catheter Implantation

All animals received care compliant with the "Principles of Laboratory Animal Care" formulated by the National Society for Medical Research and the "Guideline for the Care of Use of Laboratory Animals" prepared by the National Academy of Sciences and published by the NIH. This study was approved by the University of Michigan Committee on Use and Care of Animals.

Five adult sheep were utilized in the large animal model. All experiments were performed under sterile conditions. The first 3 sheep procedures were performed using 1% Lidocaine subcutaneously for local anesthetic. Small (1 cm to 2 cm) vertical and transverse incisions were created over the right and left jugular vein. Cannulas were then placed using a modified Seldinger technique with one cannula either control (E2As) or experimental (SNAP/E2As) placed in either the right or left jugular vein. The skin was then re-approximated using skin staples.

The final 2 sheep experiments were performed under general anesthetic. Propofol (1 mg/kg) was used for induction followed by Isoflurane (0.1-4%) anesthetic for maintenance. A small 2-3 cm incision was created overlying the jugular vein. The right and left jugular veins were then isolated and either control (E2As) or experimental (SNAP/E2As) cannulas were placed under direct visualization. Sheep were then recovered and returned to animal housing.

Animals remained in animal housing throughout the remainder of the experiment. Catheters were tested on a daily basis for patency. Cannulas were initially attempted to be aspirated and then flushed with 15 mL of saline. If aspiration was initially difficult, 15 mL of normal saline was attempted to be infused, and the process and aspiration and flushing were again tested. Patency data was recorded every 24 hour for 7 days.

Necropsy was performed on day 7. Sheep were anesthetized using the same anesthetic protocol described above. The right and left jugular veins were dissected along their length and isolated. The sheep were heparinized using approximately 100-150 IU/kg bolus dose and activated clotting time of >200 seconds was confirmed. The jugular veins were then ligated and opened longitudinally. Catheters were removed and placed in sterile saline for further analysis.

Catheter Evaluation

After explanting, the catheters were rinsed in PBS. Pictures were taken of the exterior of the whole catheter and the interior of a 1 cm piece cut longitudinally using a Nikon L24 digital camera. The degree of thrombus was quantitated using Image J imaging software from NIH. To quantitate the viable bacteria, a 1 cm piece was cut longitudinally and was homogenized in 1 mL PBS buffer. The optimal homogenizing speed was found using a separate experiment where different homogenizing speeds and times were compared. The resulting homogenate was serially diluted in sterile PBS. Triplicate aliquots of each dilution (10 µL) were plated on agar plates. The agar plates were incubated at 37° C. for 24 hours, followed by calculation of colony forming units per catheter surface area ($CFU/cm^2$).

Statistical Analysis

Throughout this disclosure, data are expressed as mean±SEM (standard error of the mean). Comparison between the various SNAP/E2As and E2As control polymer groups were analyzed by a comparison of means using student's t-test. Values of $p<0.05$ were considered statistically significant for all tests.

CONCLUSIONS

Examples of the present disclosure have shown that hydrophobic polyurethanes, e.g., siloxane-based polyurethane elastomers (one example of which is the Elast-Eon™ E2As polymer) are excellent matrices to act as a reservoir for SNAP, and the resulting films can be used for the controlled release of NO and SNAP. SNAP slowly diffuses from the polymer film, and NO release from the film/coating can be initiated by light and/or thermal decomposition when blood flows through an ECC loop. A stability study demonstrates that SNAP is quite stable within the E2As matrix, even during storage for 4 months at 37° C. While the E2As polymer has excellent innate biocompatible properties on its own, incorporating SNAP into the E2As polymer matrix provides controlled delivery of NO/SNAP to further improve polymer hemocompatibility. The SNAP/E2As coated ECC loops significantly preserved platelet count and function during 4 hours of ECC blood flow, while also reducing the clot area when compared to corresponding E2As coated control loops. In addition, the NO released from SNAP/E2As catheters was able to significantly reduce thrombus and bacterial adhesion during 7 day implantation in sheep, thereby improving catheter patency. Incorporating SNAP within Elast-Eon™ E2As polymer films/coatings provides a simple way to locally deliver NO/SNAP, and has potential for improving the hemocompatibility of a wide variety of blood-contacting medical devices.

In summary, examples as disclosed herein include novel nitric oxide (NO) releasing coatings including siloxane-based polyurethane elastomers doped with S-nitroso-N-acetylpenicillamine (SNAP) to prevent thrombus formation in, e.g., extracorporeal circulation (ECC) circuits and catheter tubing. In addition, the NO release from these formulations is likely to serve as a very effective bacterial agent.

It is to be understood that the ranges provided herein include the stated range and any value or sub-range within the stated range. For example, a range of about $0.2 \times 10^{-10}$ mol $cm^{-2}$ $min^{-1}$ to about $20 \times 10^{-10}$ mol $cm^{-2}$ $min^{-1}$ should be interpreted to include not only the explicitly recited limits of $0.2 \times 10^{-10}$ mol $cm^{-2}$ $min^{-1}$ to about $20 \times 10^{-10}$ mol $cm^{-2}$ $min^{-1}$, but also to include individual values therebetween, such as $1 \times 10^{-10}$ mol $cm^{-2}$ $min^{-1}$, $14.5 \times 10^{-10}$ mol $cm^{-2}$ $min^{-1}$, etc., as well as sub-ranges therebetween, such as from $0.75 \times 10^{-10}$ mol $cm^{-2}$ $min^{-1}$ to about $17 \times 10^{-10}$ mol $cm^{-2}$ $min^{-1}$, from about $5 \times 10^{-10}$ mol $cm^{-2}$ $min^{-1}$ to about $15 \times 10^{-10}$ mol $cm^{-2}$ $min^{-1}$, etc. Furthermore, when "about" or "approximately" or the like is/are utilized to describe a value, this is meant to encompass minor variations (up to +/−10%) from the stated value.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

Furthermore, in describing and claiming the examples disclosed herein, the singular forms "a", "an", and "the" include plural referents unless the context clearly dictates otherwise.

While several examples have been described in detail, it will be apparent to those skilled in the art that the disclosed examples may be modified. Therefore, the foregoing description is to be considered non-limiting.

What is claimed is:

1. A polymeric film, consisting of:
   a polymer matrix; and
   a discrete RSNO adduct introduced into the polymeric matrix;
   wherein the discrete RSNO adduct is S-nitroso-N-acetyl-penicillamine (SNAP) present in an amount ranging from about 5 wt % to about 10 wt % and includes SNAP crystals, wherein the discrete RSNO adduct is capable of releasing nitric oxide (NO), and wherein the polymer matrix is a polyurethane polymer matrix, a silicone rubber polymer matrix, a thermoplastic silicone-polycarbonate-urethane, a poly(vinyl chloride) polymer matrix, or a siloxane-based polyurethane elastomer;
   the polymeric film to exhibit stability under dry conditions at 37° C. and controllable NO release rates over at least a 7 day period, when exposed to moisture or light capable of photolyzing an RSNO bond, from the discrete RSNO adduct.

2. The polymeric film as defined in claim 1 wherein the polymer matrix comprises a hydrophobic polymer selected from the group consisting of the silicone rubber having water uptake of 1.2 wt %±0.3, the thermoplastic silicone-polycarbonate-urethane having water uptake of 1.5 wt %±0.3, the siloxane-based polyurethane elastomer having water uptake of 1.2 wt %±0.1; and the polyurethane polymer having water uptake of 6.2 wt %±0.7.

3. The polymeric film as defined in claim 1 wherein:
   the polymer matrix is the siloxane-based polyurethane elastomer;
   the SNAP is present in an amount of about 10 wt %; and
   wherein NO is released over at least 20 days.

4. The polymeric film as defined in claim 1 wherein the discrete RSNO adduct is dispersed within the polymer matrix, and wherein the discrete RSNO adduct is present in an amount of about 5 wt %.

5. The polymeric film as defined in claim 1 wherein the discrete RSNO adduct is dispersed within the polymer matrix, and wherein the discrete RSNO adduct is present in an amount of about 10 wt %.

6. A polymeric composition, comprising:
   a base polymer layer;
   a top polymer layer disposed on the base polymer layer; and
   at least one active layer intermediate to the base polymer layer and the top polymer layer, and the at least one active intermediate layer including the polymeric film as defined in claim 3.

7. The polymeric composition as defined in claim 6 wherein:
   the base polymer layer is selected from a siloxane-based polyurethane elastomer, poly(vinyl chloride), crosslinked polyurethane, crosslinked silicone rubber, and polytetrafluoroethylene; and the top polymer layer is a siloxane-based polyurethane elastomer, poly(vinyl chloride), crosslinked polyurethane, crosslinked silicone rubber, and polytetrafluoroethylene.

8. The polymeric film as defined in claim 1 wherein:
the polymer matrix is the siloxane-based polyurethane elastomer; and
the SNAP is present in an amount of about 5 wt %.

9. The polymeric film as defined in claim 4 wherein the polymer matrix is the siloxane-based polyurethane elastomer or the poly(vinyl chloride) polymer matrix.

\* \* \* \* \*